(12) United States Patent
Kim et al.

(10) Patent No.: US 7,390,809 B2
(45) Date of Patent: Jun. 24, 2008

(54) BETA-AMINO HETEROCYCLIC DIPEPTIDYL PEPTIDASE INHIBITORS FOR DIABETES

(75) Inventors: Dooseop Kim, Westfield, NJ (US); Jennifer E. Kowalchick, Clark, NJ (US)

(73) Assignee: Merck & Co., Inc., Rahway, NJ (US)

( * ) Notice: Subject to any disclaimer, the term of this patent is extended or adjusted under 35 U.S.C. 154(b) by 506 days.

(21) Appl. No.: 10/530,215

(22) PCT Filed: Oct. 3, 2003

(86) PCT No.: PCT/US03/31287

§ 371 (c)(1),
(2), (4) Date: Apr. 4, 2005

(87) PCT Pub. No.: WO2004/032836

PCT Pub. Date: Apr. 22, 2004

(65) Prior Publication Data

US 2006/0014953 A1    Jan. 19, 2006

Related U.S. Application Data

(60) Provisional application No. 60/416,558, filed on Oct. 7, 2002.

(51) Int. Cl.
C07D 487/04 (2006.01)
A61K 31/5025 (2006.01)
A61P 3/10 (2006.01)

(52) U.S. Cl. .......................... 514/249; 544/350
(58) Field of Classification Search ................ 544/350; 514/249
See application file for complete search history.

(56) References Cited

U.S. PATENT DOCUMENTS

| | | | |
|---|---|---|---|
| 4,386,090 A | 5/1983 | Moinet et al. | |
| 5,939,560 A | 8/1999 | Jenkins et al. | |
| 6,011,155 A | 1/2000 | Villhauer | |
| 6,166,063 A | 12/2000 | Villhauer | |
| 6,303,661 B1 | 10/2001 | Demuth et al. | |
| 6,429,313 B2 | 8/2002 | Carpino et al. | |
| 6,432,969 B1 | 8/2002 | Villhauer | |
| 6,699,871 B2 | 3/2004 | Edmondson et al. | |

FOREIGN PATENT DOCUMENTS

| | | |
|---|---|---|
| WO | WO 97/40832 | 11/1997 |
| WO | WO 98/19998 | 5/1998 |
| WO | WO 98/19998 A2 | 5/1998 |
| WO | WO 98/19998 A3 | 5/1998 |
| WO | WO 00/34241 | 6/2000 |
| WO | WO 01/34594 A1 | 5/2001 |
| WO | WO 01/42262 | 6/2001 |
| WO | WO 01/42262 A2 | 6/2001 |
| WO | WO 01/96295 A2 | 12/2001 |
| WO | WO 01/96295 A3 | 12/2001 |
| WO | WO 02/02560 A2 | 1/2002 |
| WO | WO 02/02560 A3 | 1/2002 |
| WO | WO 02/076450 A1 | 10/2002 |
| WO | WO 03/000180 A2 | 1/2003 |
| WO | WO 03/000180 A3 | 1/2003 |
| WO | WO 03/000181 A2 | 1/2003 |
| WO | WO 03/000181 A3 | 1/2003 |
| WO | WO 03/004498 A1 | 1/2003 |
| WO | WO 03/082817 A2 | 10/2003 |
| WO | WO 2004/007468 | 1/2004 |
| WO | WO 2004/007468 A1 | 1/2004 |
| WO | WO 2004/032836 A2 | 4/2004 |
| WO | WO 2004/043940 | 5/2004 |
| WO | WO 2004/043940 A1 | 5/2004 |
| WO | WO 2004/005022 A2 | 6/2004 |
| WO | WO 2004/050022 A2 | 6/2004 |
| WO | WO 2004/058266 A1 | 7/2004 |
| WO | WO 2004/064778 A2 | 8/2004 |
| WO | WO 2004/069162 A2 | 8/2004 |
| WO | WO 2004/110436 | 12/2004 |
| WO | WO 2004/110436 A1 | 12/2004 |
| WO | WO 2004/112701 A2 | 12/2004 |
| WO | WO 2004/112701 A3 | 12/2004 |
| WO | WO 2005/011581 A2 | 2/2005 |
| WO | WO 2005/044195 A2 | 5/2005 |

OTHER PUBLICATIONS

A.R. Katritsky, (ed.), Comprehensive Heterocyclic Chemistry, vol. 8, Part 6, p. 969 (1984).*

(Continued)

*Primary Examiner*—Mark L Berch
(74) *Attorney, Agent, or Firm*—Philippe L. Durette; Catherine D. Fitch

(57) ABSTRACT

The present invention is directed to compounds of structural formula (I) which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved

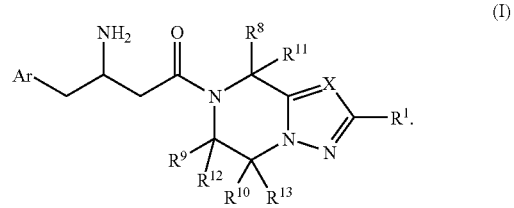

(I)

22 Claims, No Drawings

OTHER PUBLICATIONS

J.J. Holst, "Treatment of Type 2 Diabetes Mellitus with Agonists of the GLP-1 Receptor or DPP-IV Inhibitors", Expert Opin. Emerg. Drugs, vol. 9(1) pp. 155-166, 2004.

C. F. Deacon, et al., "Inhibitors of dipeptidyl peptidase IV: A Novel Approach for the Prevention and Treatment of Type 2 Diabetes?", Expert Opin. Investig. Drugs, vol. 13(9) pp. 1091-1102, 2004.

K. Augustyns et al., "Dipeptidyl Peptidase IV Inhibitors as New Therapeutic Agents for the Treatment of Type 2 Diabetes", Expert Opin. Ther. Patents, vol. 13(4), pp. 499-510, 2003.

Novartis AG: WO0034241, "Novel N-substituted-2-Cyanopyrrolidines as Potent Inhibitors of Dipeptidyl Peptidase IV in the Treatment of Non-Insulin-Dependent Diabetes Mellitus", Exp. Opin. Ther. Patents, vol. 10(12), pp. 1937-1942, 2000.

O. J. Orucker, "Therapeutic potential of dipeptidyl peptidase IV inhibitors for the treatment of type 2 diabetes", Exp. Opin Invest. Drugs, vol. 12, 2004, pp. 87-100.

T. P. Vahl & D. A. D'Alessio, "Gut peptides in the treatment of diabetes mellitus" Exp. Opin. Invest. Drugs, vol. 13, 2004, pp. 177-188.

L. B. Knudsen, "Glucagon-like peptide-1: The Basis of a New Class of Treatment for Type 2 Diabetes", J. Med. Chem, vol. 47, 2004, pp. 4128-4134.

Ann E. Weber, "Dipeptidyl Peptidase IV Inhibitors for the Treatment of Diabetes", J. Med. Chem, vol. 47, 2004, pp. 4135-4141.

J. J. Holst and C. F. Deacon, "Glucagon-like peptide 1 and inhibitors of dipeptidyl peptidase IV in the treatment of type 2 diabetes mellitus", Curr. Opin Pharmacology, vol. 4, 2004, pp. 589-596.

C. F. Deacon, "Perspectives in Diabetes—Therapeutic Strategies Based on Glucagon-Like Peptide 1", Diabetes, vol. 53, Sep. 2004, pp. 2181-2189.

Augustyns, K. et al., "Dipeptidyl peptidase IV inhibitors as new therapeutic agents for the treatment of Type 2 diabetes" Expert Opin. Ther. Patents, vol. 13, No. 4, pp. 499-510, 2003.

Deacon, C. F. et al., "Inhibitors of dipeptidyl peptidase IV: a novel approach for the prevention and treatment of Type 2 diabetes?" Expert Opin. Investig. Drugs, vol. 13, No. 9, pp. 1091-1102, 2004.

Deacon, C. F., "Perspectives in Diabetes—Therapeutic Strategies Based on Glucagon-Like Peptide 1" Diabetes, vol. 53, pp. 2181-2189, 2004.

Drucker, D. J., "Therapeutic potential of dipeptidyl peptidase IV inhibitors for the treatment of type 2 diabetes" Expert Opin. Investig. Drugs, vol. 12, No. 1, pp. 87-100, 2003.

Holst, J. J., "Treatment of Type 2 diabetes mellitus with agonists of the GLP-1 receptor or DPP-IV inhibitors" Expert Opin. Emerg. Drugs, vol. 9, No. 1, pp. 155-166, 2004.

Holst, J. J. et al., "Glucagon-like peptide 1 and inhibitors of dipeptidyl peptidase IV in the treatment of type 2 diabetes mellitus" Current Opinion in Pharmacology, vol. 4, pp. 589-596, 2004.

Knudsen, L. B., "Glucagon-like Peptide-1: The Basis of a New Class of Treatment for Type 2 Diabetes" J. Med. Chem, vol. 47, pp. 4128-4134, 2004.

Stockel-Maschek, A. et al., "Potent Inhibitors of Dipeptidyl Peptidase IV and their Mechanisms of Inhibition" Cellular Peptidases in Immune Functions and Diseases 2, vol. 477, pp. 117-123, 2000.

Novartis AG: WO0034241 "Novel N-substituted-2-cyanopyrrolidines as potent inhibitors of dipeptidyl peptidase IV in the treatment of non-insulin-dependent diabetes mellitus" Exp. Opin. Ther. Patents, vol. 10, No. 12, pp. 1937-1942, 2000.

Vahl, T. P. et al., "Gut peptides in the treatment of diabetes mellitus" Expert Opin. Investig. Drugs, vol. 13, No. 3, pp. 177-188, 2004.

Weber, A. E., "Dipeptidyl Peptidase IV Inhibitors for the Treatment of Diabetes", J. Med. Chem., vol. 47, pp. 4135-4141, 2004.

* cited by examiner

BETA-AMINO HETEROCYCLIC DIPEPTIDYL PEPTIDASE INHIBITORS FOR DIABETES

CROSS REFERENCE TO RELATED APPLICATIONS

This application is the National Stage of International Application No. PCT/US03/31287, filed 03 Oct. 2003, which claims the benefit under 35 U.S.C. 119(e) of U.S. Provisional Application No. 60/416,558, filed 07 Oct. 2002.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly type 2 diabetes. See for example WO 97/40832, WO 98/19998, U.S. Pat. No. 5,939,560, *Bioorg. Med. Chem. Lett.*, 6: 1163-1166 (1996); and *Bioorg. Med. Chem. Lett.*, 6: 2745-2748 (1996). The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors also have other therapeutic utilities, as discussed herein. DP-IV inhibitors have not been studied extensively to date, especially for utilities other than diabetes. New compounds are needed so that improved DP-IV inhibitors can be found for the treatment of diabetes and potentially other diseases and conditions. The therapeutic potential of DP-IV inhibitors for the treatment of type 2 diabetes is discussed by D. J. Drucker in *Exp. Opin. Invest. Drugs*, 12: 87-100 (2003) and by K. Augustyns, et al., in *Exp. Opin. Ther. Patents*, 13: 499-510 (2003).

SUMMARY OF THE INVENTION

The present invention is directed to compounds which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to heterocyclic compounds useful as inhibitors of dipeptidyl peptidase-IV. Compounds of the present invention are described by structural formula I:

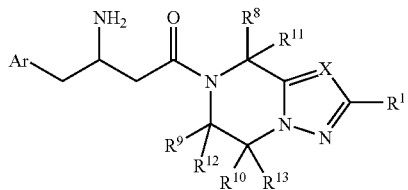

(I)

or a pharmaceutically acceptable salt thereof; wherein
each n is independently 0, 1, or 2;
X is N or $CR^{2-}$;
Ar is phenyl substituted with one to five $R^3$ substituents;
$R^1$ and $R^2$ are each independently selected from the group consisting of
hydrogen,
halogen,
cyano,
$C_{1-10}$ alkyl, wherein alkyl is unsubstituted or substituted with one to five halogens,
$C_{1-10}$ alkoxy, wherein alkoxy is unsubstituted or substituted with one to five substituents independently selected from halogen or hydroxy,
$C_{1-10}$ alkylthio, wherein alkylthio is unsubstituted or substituted with one to five substituents independently selected from halogen or hydroxy,
$C_{2-10}$ alkenyl, wherein alkenyl is unsubstituted or substituted with one to five substituents independently selected from halogen or hydroxy,
$(CH_2)_n COOH$,
$(CH_2)_n COOC_{1-6}$ alkyl,
$(CH_2)_n CONR^4R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
$(CH_2)_n$—$NR^4R^5$,
$(CH_2)_n$—$OCONR^4R^5$,
$(CH_2)_n$—$SO_2NR^4R^5$,
$(CH_2)_n$—$SO_2R^6$,
$(CH_2)_n$—$NR^7SO_2R^6$,
$(CH_2)_n$—$NR^7CONR^4R^5$,
$(CH_2)_n$—$NR^7COR^7$,
$(CH_2)_n$—$NR^7CO_2R^6$,
$(CH_2)_n$—$COR^6$,
$(CH_2)_n$-aryl, wherein aryl is unsubstituted or substituted with one to five substituents independently selected from halogen, CN, hydroxy, $NR^7SO_2R^6$, $SO_2R^6$, $CO_2H$, $C_{1-6}$ alkyloxycarbonyl, $C_{1-6}$ alkyl and $C_{1-6}$ alkoxy, wherein alkyl and alkoxy are unsubstituted or substituted with one to five substituents independently selected from halogen, $CO_2H$, and $C_{1-6}$ alkyloxycarbonyl,
$(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens,
$(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens; and
wherein any methylene ($CH_2$) carbon atom in $R^1$ or $R^2$ is unsubstituted or substituted with one to two groups independently selected from halogen, hydroxy, and $C_{1-4}$ alkyl unsubstituted or substituted with one to five halogens;
each $R^3$ is independently selected from the group consisting of
hydrogen,
halogen,
cyano,
hydroxy,
$C_{1-6}$ alkyl, unsubstituted or substituted with one to five halogens, and
$C_{1-6}$ alkoxy, unsubstituted or substituted with one to five halogens;
$R^6$ is independently selected from the group consisting of tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $R^6$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;
each $R^7$ is hydrogen or $R^6$;
$R^8, R^9, R^{10}, R^{11}, R^{12}$, and $R^{13}$ are each independently selected from the group consisting of:
hydrogen, cyano,
$(CH_2)_nCOOH$,
$(CH_2)_nCOOC_{1-6}$ alkyl, wherein alkyl is unsubstituted or substituted with one to three substituents independently selected from halogen and phenyl,
$C_{1-10}$ alkyl, unsubstituted or substituted with one to five substituents independently selected from halogen, hydroxy, $C_{1-6}$ alkoxy, carboxy, $C_{1-6}$ alkyloxycarbonyl, and phenyl-$C_{1-3}$ alkoxy, wherein alkoxy is unsubstituted or substituted with one to five halogens,
$(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens,
$(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_nCONR^4R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or wherein $R^4$ and $R^5$ together with the nitrogen atom to which they are attached form a heterocyclic ring selected from azetidine, pyrrolidine, piperidine, piperazine and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; and
wherein any methylene ($CH_2$) carbon atom in $R^8$, $R^9$, $R^{10}$, $R^{11}$, $R^{12}$, or $R^{13}$ is unsubstituted or substituted with one to two groups independently selected from halogen, hydroxy, and $C_{1-4}$ alkyl unsubstituted or substituted with one to five halogens.

In one embodiment of the compounds of the present invention, the carbon atom marked with an * has the R configuration as depicted in formula Ia

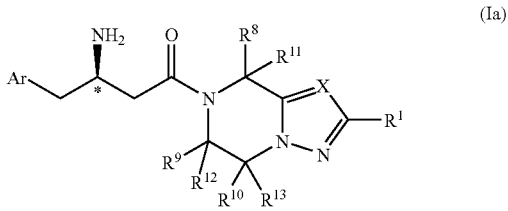
(Ia)

wherein Ar, X, $R^1$, $R^8$, $R^9$, $R^{10}$, $R^{11}$, $R^{12}$ and $R^{13}$ are as defined herein.

In a second embodiment of the compounds of the present invention, X is N as depicted in formula Ib:

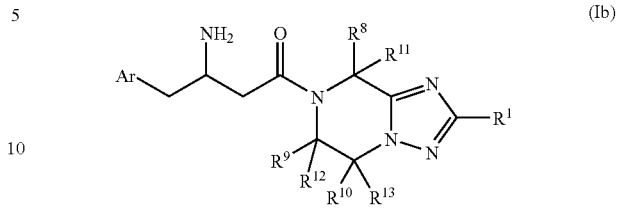
(Ib)

wherein Ar, $R^1$, $R^8$, $R^9$, $R^{10}$, $R^{11}$, $R^{12}$, and $R^{13}$ are as defined herein.

In a class of this second embodiment, the carbon atom marked with an * has the R configuration as depicted in formula Ic:

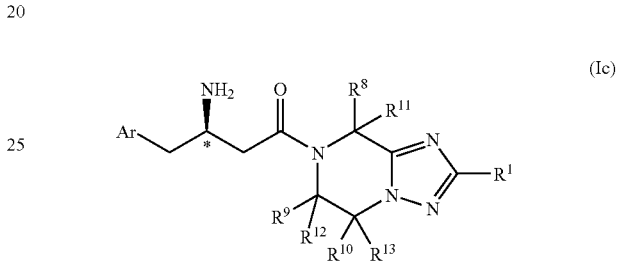
(Ic)

wherein Ar, $R^1$, $R^8$, $R^9$, $R^{10}$, $R^{11}$, $R^{12}$, and $R^{13}$ are as defined herein.

In another class of this second embodiment of the compounds of the present invention, $R^9$, $R^{10}$, $R^{11}$, $R^{12}$, and $R^{13}$ are hydrogen as depicted in formula Id:

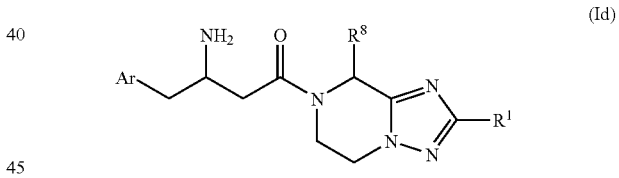
(Id)

wherein Ar, $R^1$, and $R^8$ are as defined herein.

In a third embodiment of the compounds of the present invention, X is $CR^2$ as depicted in formula Ie:

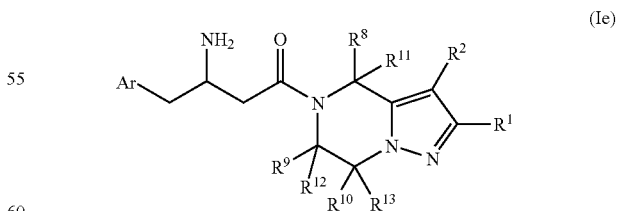
(Ie)

wherein Ar, $R^1$, $R^2$, $R^8$, $R^9$, $R^{10}$, $R^1$, $R^{12}$, and $R^{13}$ are as defined herein.

In a class of this third embodiment, the carbon atom marked with an * has the R configuration as depicted in formula If:

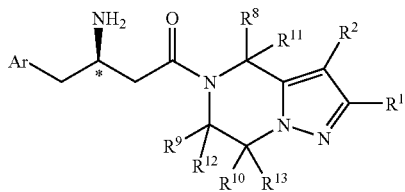

(If)

wherein Ar, $R^1$, $R^2$, $R^8$, $R^9$, $R^{10}$, $R^{11}$, $R^{12}$, and $R^{13}$ are as defined herein.

In another class of this third embodiment of the compounds of the present invention, $R^9$, $R^{10}$, $R^{11}$, $R^{12}$ and $R^{13}$ are hydrogen as depicted in formula Ig:

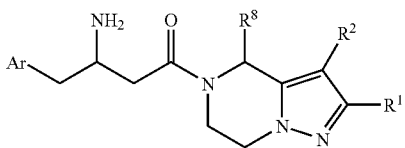

(Ig)

wherein Ar, $R^1$, $R^2$, and $R^8$ are as defined herein.

In a fourth embodiment of the compounds of the present invention, $R^3$ is selected from the group consisting of hydrogen, fluoro, chloro, bromo, trifluoromethyl, and methyl. In a class of this embodiment, $R^3$ is selected from the group consisting of hydrogen, fluoro, and chloro. In a subclass of this class, $R^3$ is hydrogen or fluoro.

In a fifth embodiment of the compounds of the present invention, $R^1$ is selected from the group consisting of:
hydrogen,
$C_{1-6}$ alkyl, wherein alkyl is unsubstituted or substituted with one to five fluorines,
$(CH_2)_n$-phenyl wherein phenyl is unsubstituted or substituted with one to five substituents independently selected from hydroxy, halogen, $C_{1-6}$ alkyl, $C_{1-6}$ alkoxy, wherein alkyl and alkoxy are unsubstituted or substituted with one to five halogens,
$C_{3-6}$ cycloalkyl, unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; and
wherein any methylene ($CH_2$) carbon atom in $R^1$ is unsubstituted or substituted with one to two groups independently selected from halogen, hydroxy, and $C_{1-4}$ alkyl unsubstituted or substituted with one to five halogens.

In a class of this embodiment of the compounds of the present invention, $R^1$ is selected from the group consisting of
hydrogen,
methyl,
ethyl,
difluoromethyl,
trifluoromethyl,
$CH_2CF_3$,
$CF_2CF_3$,
phenyl, and
cyclopropyl.

In a subclass of this class, $R^1$ is selected from the group consisting of hydrogen, difluoromethyl, trifluoromethyl, phenyl, and cyclopropyl.

In a sixth embodiment of the compounds of the present invention, $R^2$ is selected from the group consisting of
hydrogen,
$C_{1-6}$ alkyl, unsubstituted or substituted with one to five fluorines, phenyl, unsubstituted or substituted with one to three substituents independently selected from fluoro, chloro, trifluoromethyl, methoxy, and $OCF_3$, and
$C_{3-6}$ cycloalkyl, unsubstituted or substituted with one to five substituents independently selected from halogen, hydroxy, $C_{1-6}$ alkyl, and
$C_{1-6}$ alkoxy, wherein alkyl and alkoxy are unsubstituted or substituted with one to five halogens.

In a class of this embodiment of the compounds of the present invention, $R^2$ is selected from the group consisting of hydrogen, trifluoromethyl, phenyl, and cyclopropyl. In a subclass of this class, $R^2$ is hydrogen or trifluoromethyl.

In a seventh embodiment of the compounds of the present invention, $R^{11}$, $R^{12}$, and $R^{13}$ are each hydrogen and $R^8$, $R^9$, and $R^{10}$ are each independently selected from the group consisting of:
hydrogen,
$C_{1-6}$ alkyl, unsubstituted or substituted with one to five substituents independently selected from halogen, hydroxy, $C_{1-6}$ alkoxy, and phenyl-$C_{1-3}$ alkoxy, wherein alkoxy is unsubstituted or substituted with one to five halogens,
$(CH_2)_n$COOH,
$(CH_2)_n$COOC$_{1-6}$ alkyl, wherein alkyl is unsubstituted or substituted with one to three substituents independently selected from halogen and phenyl,
$(CH_2)_n$CONR$^4$R$^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or wherein $R^4$ and $R^5$ together with the nitrogen atom to which they are attached form a heterocyclic ring selected from azetidine, pyrrolidine, piperidine, piperazine and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$-phenyl, wherein phenyl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens,
$(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are optionally substituted with one to five halogens; and wherein any methylene ($CH_2$) carbon atom in $R^8$, $R^9$ or $R^{10}$ is unsubstituted or substituted with one to two groups independently selected from halogen, hydroxy, and $C_{1-4}$ alkyl unsubstituted or substituted with one to five halogens.

In a class of this embodiment of the compounds of the present invention, $R^8$, $R^9$, and $R^{10}$ are each independently selected from the group consisting of:

hydrogen, $C_{1-3}$ alkyl, unsubstituted or substituted with one to three substituents independently selected from halogen, hydroxy, $C_{1-6}$ alkoxy, and phenyl-$C_{1-13}$ alkoxy, wherein alkoxy is unsubstituted or substituted with one to five halogens, $(CH_2)_n COOH$, $(CH_2)_n COOC_{1-6}$ alkyl, wherein alkyl is unsubstituted or phenyl, $(CH_2)_n CONR^4 R^5$, wherein $R^4$ and $R^5$ are independently selected from the group consisting of hydrogen and $C_{1-6}$ alkyl, wherein alkyl is unsubstituted or substituted with one to five halogens;

or wherein $R^4$ and $R^5$ together with the nitrogen atom to which they are attached form a heterocyclic ring selected from azetidine, pyrrolidine, piperidine, piperazine and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-phenyl, wherein phenyl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are optionally substituted with one to five halogens, $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are optionally substituted with one to five halogens, $(CH_2)_n$—$C_{3-6}$ cyclopropyl; and wherein any methylene ($CH_2$) carbon atom in $R^8$, $R^9$ or $R^{10}$ is unsubstituted or substituted with one to two groups independently selected from halogen, hydroxy, and $C_{1-4}$ alkyl unsubstituted or substituted with one to five halogens.

In a subclass of this class, $R^8$, $R^9$, and $R^{10}$ are each independently selected from the group consisting of:

hydrogen, $CH_3$, $CH_2 CH_3$, $CH_2$-cyclopropyl, $CHF$-cyclopropyl, $CH(OH)$-cyclopropyl, $CH_2 OCH_2 Ph$, $CH_2(4\text{-F-Ph})$, $CH_2(4\text{-CF}_3\text{-Ph})$, $CH_2$-[1,2,4]triazol-4-yl, $CH_2$-(imidazol-1-yl), $CH_2$-(pyrazol-1-yl), $CH_2$—$COOCH_2 Ph$, $CH_2$—$COOH$, $CH_2$—$CONMe2$, and $CH_2 OCH_3$.

In a further subclass of this class, $R^9$ and $R^{10}$ are each independently hydrogen or methyl.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. "Heteroaryl" also includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-α]pyridinyl,[1,2,4-triazolo][4,3-α]pyridinyl, pyrazolo[1,5-α]pyridinyl, [1,2,4-triazolo][1,5-α]pyridinyl, 2-oxo-1,3-benzoxazolyl, 4-oxo-3H-quinazolinyl, 3-oxo-[1,2,4]-triazolo[4,3-α]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention may contain one or more asymmetric centers and can thus occur as racemates and racemic mixtures, single enantiomers, diastereomeric mixtures and individual diastereomers. The compounds of the present invention have one asymmetric center at the carbon atom marked with an * in formula Ia. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia shows the preferred sterochemistry at the carbon atom to which is attached the amino group of the beta amino acid from which these compounds are prepared.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DP-IV to release the fluorescent AMC leaving group. The kinetic parameters that describe this reaction are as follows: $K_m$=50 µM; $k_{cat}$=75 s$^{-1}$; $k_{cat}/K_m$=1.5×10$^6$ M$^{-1}$s$^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an IC$_{50}$ of less than about 1 µM. Such a result is indicative of the intrinsic activity of the compounds in use as inhibitors the dipeptidyl peptidase-IV enzyme activity.

Dipeptidyl peptidase-IV enzyme (DP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DP-IV. Studies with DP-IV$^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP). Inactivation of these peptides by DP-IV may also play a role in glucose homeostasis.

The DP-IV inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention. In Syndrome X, also known as Metabolic Syndrome, obesity is thought to promote insulin resistance, diabetes, dyslipidemia, hypertension, and increased cardiovascular risk. Therefore, DP-IV inhibitors may also be useful to treat hypertension associated with this condition.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

Obesity: DP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine*, 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (*Nature Medicine*, 6: 802-807 (2000)). In addition, studies with DP-IV deficient mice suggest that these animals are resistant to diet-induced obesity and associated pathology (e.g. hyperinsulinonemia).

Growth Hormone Deficiency: DP-IV inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF[3-44]; this is prevented by the DP-IV inhibitor diprotin A; and (3) GRF[3-44] is found in the plasma of a human GRF transgenic pig (*J. Clin. Invest.*, 83: 1533-1540 (1989)). Thus DP-IV inhibitors may be useful for the same spectrum of indications which have been considered for growth hormone secretagogues.

Intestinal Injury: The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (*Regulatory Peptides*, 90: 27-32 (2000)). Administration of GLP-2 results in increased small bowel mass in rodents and attenuates intestinal injury in rodent models of colitis and enteritis.

Immunosuppression: DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosuppressants in animal models of transplantation and arthritis. Prodipine (Pro-Pro-diphenyl-phosphonate), an irreversible inhibitor of DP-IV, was shown to double cardiac allograft survival in rats from day 7 to day 14 (*Transplantation*, 63: 1495-1500 (1997)). DP-IV inhibitors have been tested in collagen and alkyldiamine-induced arthritis in rats and showed a statistically significant attenuation of hind paw swelling in this model [*Int. J. Immunopharmacology*, 19:15-24 (1997) and *Immunopharmacology*, 40: 21-26 (1998)]. DP-IV is upregulated in a number of autoimmune diseases including rheumatoid arthritis, multiple sclerosis, Graves' disease, and Hashimoto's thyroiditis (*Immunology Today*, 20: 367-375 (1999)).

HIV Infection: DP-IV inhibition may be useful for the treatment or prevention of HIV infection or AIDS because a number of chemokines which inhibit HIV cell entry are potential substrates for DP-IV (*Immunology Today* 20: 367-375 (1999)). In the case of SDF-1alpha, cleavage decreases antiviral activity (*PNAS*, 95: 6331-6 (1998)). Thus, stabilization of SDF-1alpha through inhibition of DP-IV would be expected to decrease HIV infectivity.

Hematopoiesis: DP-IV inhibition may be useful for the treatment or prevention of hematopiesis because DP-IV may be involved in hematopoiesis. A DP-IV inhibitor, Val-Boro-Pro, stimulated hematopoiesis in a mouse model of cyclophosphamide-induced neutropenia (WO 99/56753).

Neuronal Disorders: DP-IV inhibition may be useful for the treatment or prevention of various neuronal or psychiatric disorders because a number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m$ about $10^6$ $M^{-1}s^{-1}$ or greater. In an electric shock jump test model of analgesia in rats, a DP-IV inhibitor showed a significant effect that was independent of the presence of exogenous endomorphin-2 (*Brain Research*, 815: 278-286 (1999)).

Neuroprotective and neuroregenerative effects of DP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26-29, 2002 (Berlin, Germany)].

Tumor Invasion and Metastasis: DP-IV inhibition may be useful for the treatment or prevention of tumor invasion and metastasis because an increase or decrease in expression of several ectopeptidases including DP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

Benign Prostatic Hypertrophy: DP-IV inhibition may be useful for the treatment of benign prostatic hypertrophy because increased DP-IV activity was noted in prostate tissue from patients with BPH (*Eur. J. Clin. Chem. Clin. Biochem.*, 30: 333-338 (1992)).

Sperm motility/male contraception: DP-IV inhibition may be useful for the altering sperm motility and for male contraception because in seminal fluid, prostatosomes, prostate derived organelles important for sperm motility, possess very high levels of DP-IV activity (*Eur. J. Clin. Chem. Clin. Biochem.*, 30: 333-338 (1992)).

Gingivitis: DP-IV inhibition may be useful for the treatment of gingivitis because DP-IV activity was found in gingival crevicular fluid and in some studies correlated with periodontal disease severity (*Arch. Oral Biol.*, 37: 167-173 (1992)).

Osteoporosis: DP-IV inhibition may be useful for the treatment or prevention of osteoporosis because GIP receptors are present in osteoblasts.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DP-IV) inhibitors;

(b) insulin sensitizers including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide glyburide, glipizide, glimepiride, and meglitinides, such as repaglinide;

(e) α-glucosidase inhibitors (such as acarbose and miglitol);

(f) glucagon receptor antagonists such as those disclosed in WO 98/04528, WO 99/01423, WO 00/39088, and WO 00/69810;

(g) GLP-1, GLP-1 mimetics, and GLP-1 receptor agonists such as those disclosed in WO 00/42026 and WO 00/59887;

(h) GIP and GIP mimetics such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-COA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as beta-sitosterol and ezetimibe, (vii) acyl CoA:cholesterol acyltransferase inhibitors, such as avasimibe, and (viii) anti-oxidants, such as probucol;

(k) PPARδ agonists, such as those disclosed in WO 97/28149;

(l) antiobesity compounds such as fenfluramine, dexfenfluramine, phentermine, sibutramine, orlistat, neuropeptide $Y_1$ or $Y_5$ antagonists, CB1 receptor inverse agonists and antagonists, $\beta_3$ adrenergic receptor agonists, melanocortin receptor agonists, in particular melanocortin-4 receptor agonists, ghrelin antagonists, and melanin-concentrating hormone (MCH) receptor antagonists;

(m) ileal bile acid transporter inhibitors;

(n) agents intended for use in inflammatory conditions such as aspirin, non-steroidal anti-inflammatory drugs, glucocorticoids, azulfidine, and selective cyclooxygenase-2 inhibitors;

(o) antihypertensive agents such as ACE inhibitors (enalapril, lisinopril, captopril, quinapril, tandolapril), A-II receptor blockers (losartan, candesartan, irbesartan, valsartan, telmisartan, eprosartan), beta blockers and calcium channel blockers; and (p) glucokinase activators (GKAs).

Dipeptidyl peptidase-IV inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DP-IV inhibitor compounds include isoleucine thiazolidide; NVP-DPP728; P32/98; and LAF 237.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents,* 11: 1677-1692 (2001) and D. Spanswick and K. Lee, "Emerging antiobesity drugs," *Expert Opin. Emerging Drugs,* 8: 217-237 (2003).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists," *Expert Opin. Ther. Patents,* 12: 1631-1638 (2002).

The potential utility of safe and effective activators of glucokinase (GKAs) for the treatment of diabetes is discussed in J. Grimsby et al., "Allosteric Activators of Glucokinase: Potential Role in Diabetes Therapy," *Science,* 301: 370-373 (2003).

The above combinations include combinations of a compound of the present invention not only with one other active compound, but also with two or more other active compounds. Non-limiting examples include combinations of compounds having Formula I with two or more active compounds selected from biguanides, sulfonylureas, IMG-CoA reductase inhibitors, PPAR agonists, PTP-1B inhibitors, other DP-IV inhibitors, and anti-obesity compounds.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared from beta amino acid intermediates such as those of formula II and substituted heterocyclic intermediates such as those of formula III, using standard peptide coupling conditions followed by deprotection. The preparation of these intermediates is described in the following Schemes.

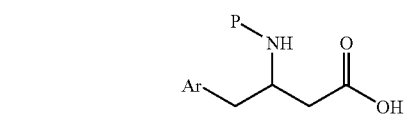

II

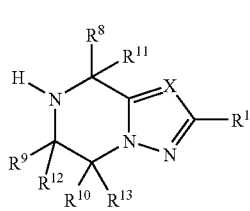

III where Ar, X, $R^1$, $R^8$, $R^9$, $R^{10}$, $R^{11}$, $R^{12}$ and $R^{13}$ are as defined above and P is a suitable nitrogen protecting group such as tert-butoxycarbonyl (BOC), benzyloxycarbonyl (Cbz), or 9-fluorenylmethoxycarbonyl (Fmoc).

SCHEME 1

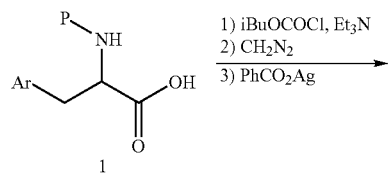

1

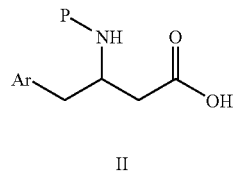

II

Compounds of formula II are commercially available, known in the literature or may be conveniently prepared by a variety of methods familiar to those skilled in the art. One common route is illustrated in Scheme 1. Protected alpha-amino acid 1, which may be commercially available or readily prepared from the corresponding amino acid by protection using, for example, di-tert-butyl-dicarbonate (for P=BOC), carbobenzyloxy chloride (for P=Cbz), or N-(9-fluorenylmethoxycarbonyloxy)succinimide (for P=Fmoc), is treated with isobutyl chloroformate and a base such as triethylamine or diisopropylethylamine, followed by diazomethane. The resultant diazoketone is then treated with silver benzoate in a solvent such as methanol or aqueous dioxane and may be subjected to sonication following the procedure of Sewald et al., *Synthesis,* 837 (1997) in order to provide the beta amino acid II. As will be understood by those skilled in the art, for the preparation of enantiomerically pure beta amino acids II, enantiomerically pure alpha amino acids 1 may be used. Alternate routes to the protected beta-amino acid intermediates II can be found in the following reviews: E. Juaristi, *Enantioselective Synthesis of β-Amino Acids*, Ed., Wiley-VCH, New York: 1997; Juaristi et al., *Aldrichimica Acta,* 27: 3 (1994); and Cole et al., *Tetrahedron,* 32: 9517 (1994).

SCHEME 2

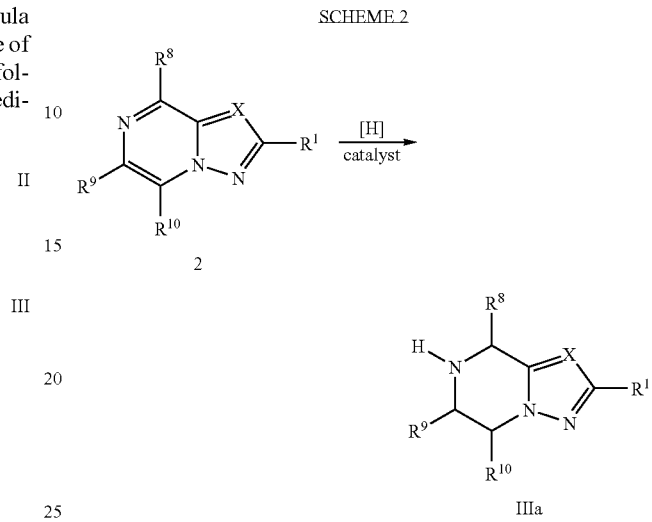

IIIa

The optionally substituted heterocyclic intermediates of formula III are commercially available, known in the literature or may be conveniently prepared by a variety of methods familiar to those skilled in the art. One convenient method for the synthesis of IIIa wherein $R^{11}$, $R^{12}$ and $R^{13}$ are hydrogen is shown in Scheme 2. Unsaturated derivative 2 is reduced, for example, by treatment with hydrogen gas and a catalyst such as palladium on carbon or platinum oxide in a solvent such as methanol or ethanol to provide Compound IIIa.

SCHEME 3

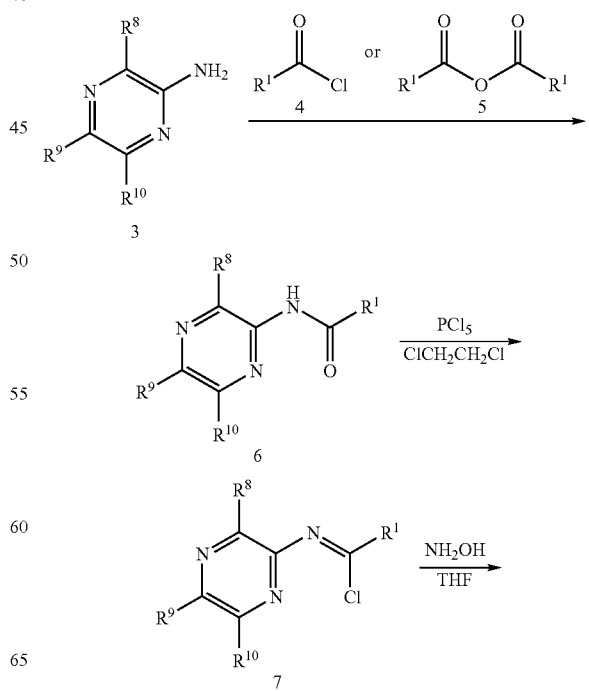

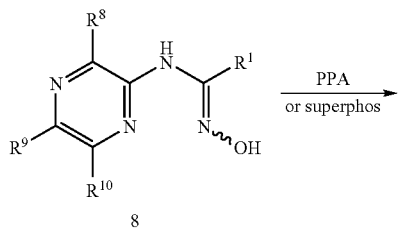

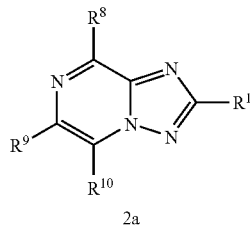

Intermediate 2 is commercially available, known in the literature or may be conveniently prepared by a variety of methods familiar to those skilled in the art. One convenient method for Intermediates 2a, wherein X is N, is illustrated in Scheme 3. Aminopyrazine 3, which is commercially available, known in the literature or may be conveniently prepared by a variety of methods familiar to those skilled in the art, is treated with an activated carboxylate derivative such as acid chloride 4 or anhydride 5, conveniently in the presence of a base such as triethylamine in a solvent such as dichloromethane, to provide amide 6. The amide is treated with phosphorus pentachloride at elevated temperatures, conveniently in refluxing dichloroethane, to provide the imidoyl chloride 7. Treatment with hydroxylamine provides intermediate 8, which may be cyclized to the desired heterocycle 2a by heating in polyphosphoric acid (PPA) or superphosphoric acid (superphos).

SCHEME 4

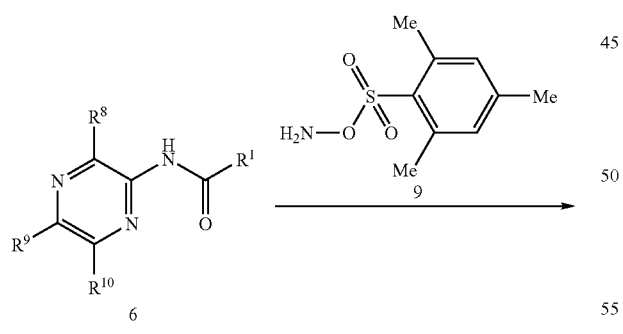

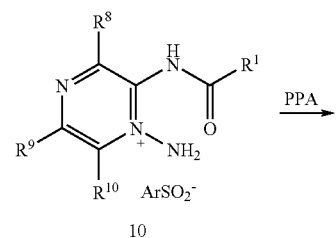

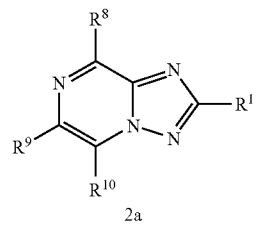

An alternate route to heterocycle 2a, wherein X is N, is shown in Scheme 4. Intermediate 6, prepared as described above in Scheme 3, is treated with an aminating reagent such as O-trimethylbenzenesulfonylhydroxylamine (9) to provide the aminopyrazonium salt 10. Cyclization with PPA provides heterocycle 2a.

SCHEME 5

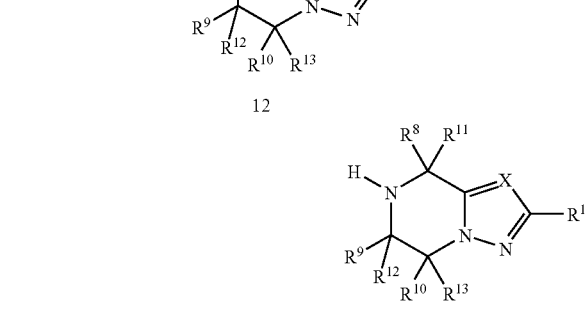

An alternate method for preparing heterocycle III, wherein $R^8$ is not H, is illustrated in Scheme 5. Heterocycle IIIb is protected, for example, as a carbamate such as a tert-butyl carbamate (BOC) by treatment with di-tert-butyl dicarbonate to provide carbamate 11. Following deprotonation with a strong base such as sec-butyl lithium or n-butyl lithium in the presence of TMEDA, the resultant anion is treated with an electrophile such as an alkyl halide or aldehyde to provide heterocycle 12. The process may be repeated to install a second alkyl group, $R^{11}$. The carbamate protecting group is then removed, in the case of BOC, by treatment with an acid such as hydrogen chloride in methanol or trifluoroacetic acid in dichloromethane, to provide the desired heterocycle III.

SCHEME 6

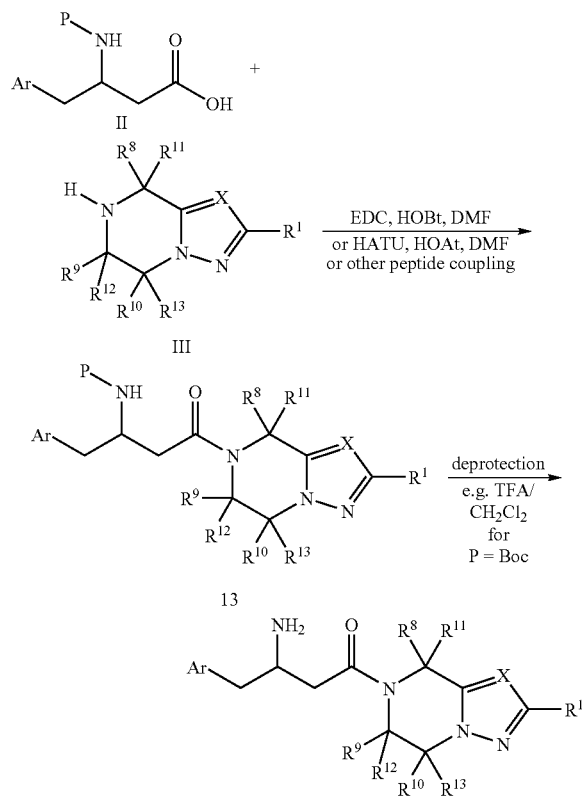

Intermediates II and III are coupled under standard peptide coupling conditions, for example, using 1-ethyl-3-(3-dimethylaminopropyl)carbodiimide and 1-hydroxybenzotriazole (EDC/HOBT) or O-(7-azabenzotriazol-1-yl)-N,N,N',N'-tetramethyluronium hexafluorophosphate and 1-hydroxy-7-azabenzotriazole (HATU/HOAT) in a solvent such as N,N-dimethylformamide (DMF) or dichloromethane for 3 to 48 hours at ambient temperature to provide Intermediate 13 as shown in Scheme 6. In some cases, Intermediate III may be a salt, such as a hydrochloride or trifluoroacetic acid salt, and in these cases it is convenient to add a base, generally N,N-diisopropylethylamine, to the coupling reaction. The protecting group is then removed with, for example, trifluoroacetic acid or methanolic hydrogen chloride in the case of Boc to give the desired amine I. The product is purified from unwanted side products, if necessary, by recrystallization, trituration, preparative thin layer chromatography, flash chromatography on silica gel, such as with a Biotage® apparatus, or HPLC. Compounds that are purified by HPLC may be isolated as the corresponding salt. Purification of intermediates is achieved in the same manner.

In some cases the product I, prepared as described in Scheme 6, may be further modified, for example, by manipulation of substituents on X, $R^1$, $R^8$, $R^9$, $R^{10}$, $R^{11}$, $R^{12}$, or $R^{13}$. These manipulations may include, but are not limited to, reduction, oxidation, alkylation, acylation, and hydrolysis reactions which are commonly known to those skilled in the art.

SCHEME 7

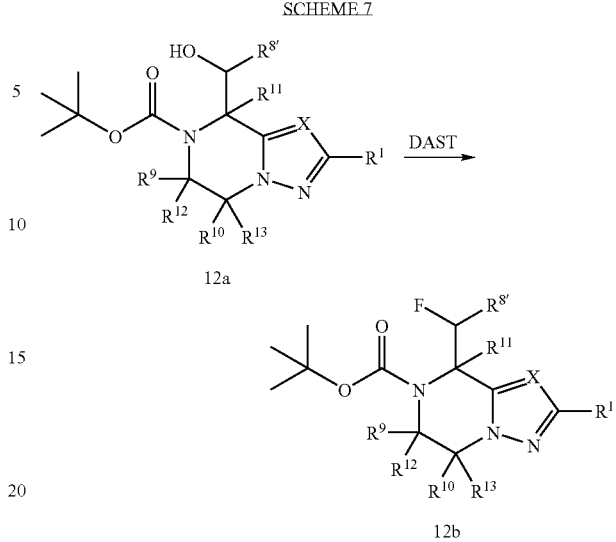

In some cases intermediates described in the above schemes may be further modified before the sequences are completed, for example, by manipulation of substituents on X, $R^1$, $R^8$, $R^9$, $R^{10}$, $R^{11}$, $R^{12}$, or $R^{13}$. These manipulations may include, but are not limited to, reduction, oxidation, alkylation, acylation, and hydrolysis reactions which are commonly known to those skilled in the art. One such example is illustrated in Scheme 7. Intermediate 12a, wherein $R^8$ contains a hydroxyl group, may be treated with (diethylamino)sulfur trifluoride (DAST) to provide the fluoro intermediate 12b. Intermediate 12b is converted to Intermediate III as described in Scheme 5.

SCHEME 8

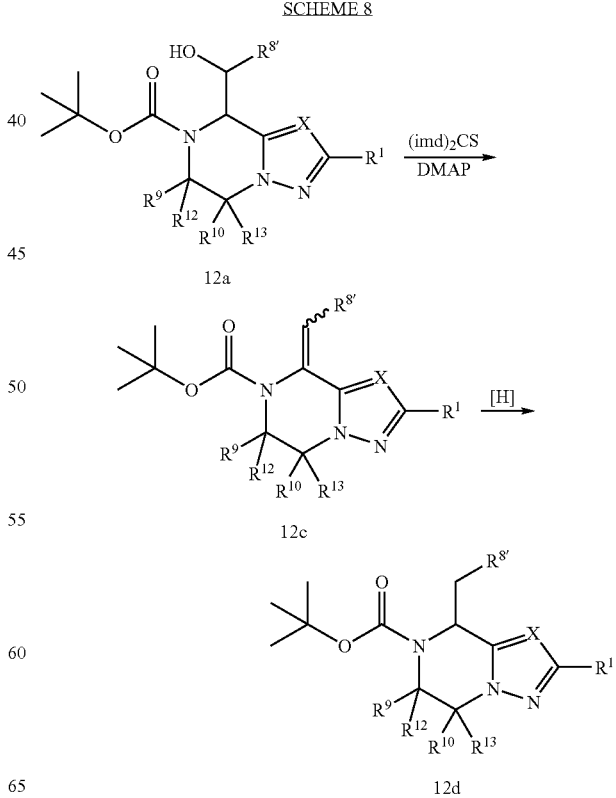

Another example is illustrated in Scheme 8. Intermediate 12a, wherein $R^8$ is $CHOHR^{8'}$, is dehydrated, conveniently by treatment with 1,1-thiocarbonyldiimidazole in the presence of a catalytic amount of dimethylaminopyridine (DMAP), to give olefin 12c. Reduction of the olefin, for example by treatment with hydrogen over a catalyst such as palladium on carbon, provides the desired intermediate 12d. Intermediate 12d is converted to Intermediate III as described in Scheme 5.

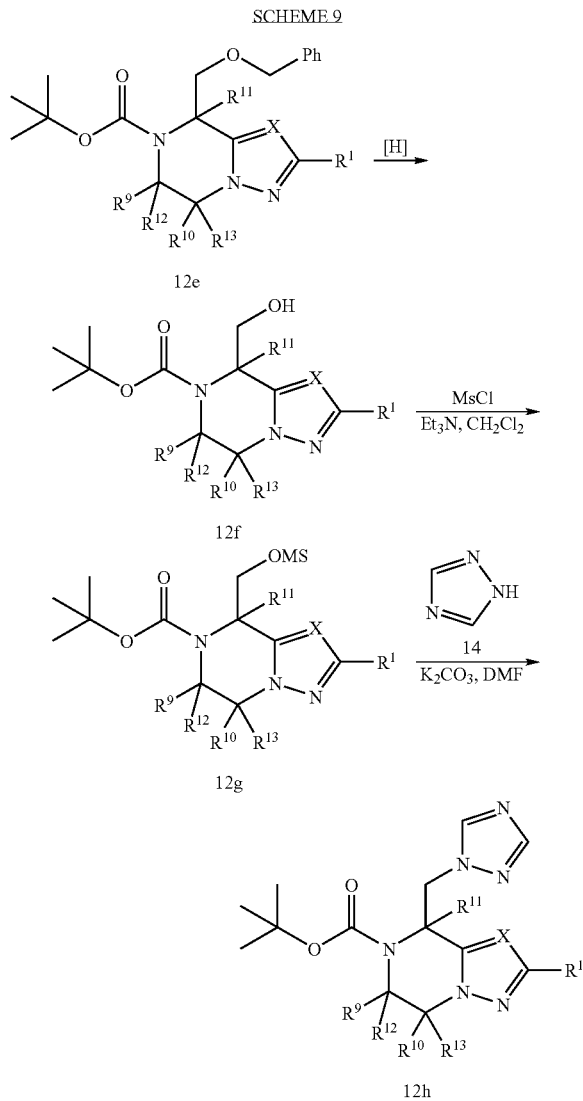

Scheme 9 illustrates another such example. Intermediate 12e wherein $R^8$ is benzyloxymethyl is reductively hydrogenated, for example, by treatment with hydrogen in the presence of a catalyst such as palladium on carbon, to provide alcohol 12f. The alcohol is converted to the corresponding mesylate 12g by treatment with mesyl chloride and a base such as triethylamine. The mesylate may be displaced with a variety of electrophiles, conveniently in the presence of a base. One such electrophile, illustrated in Scheme 9, is triazole 14, which may be reacted in the presence of potassium carbonate in a solvent such as N,N-dimethylformamide to provide the triazolylmethyl intermediate 12h. Intermediate 12h is converted into Intermediate III as described in Scheme 5.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

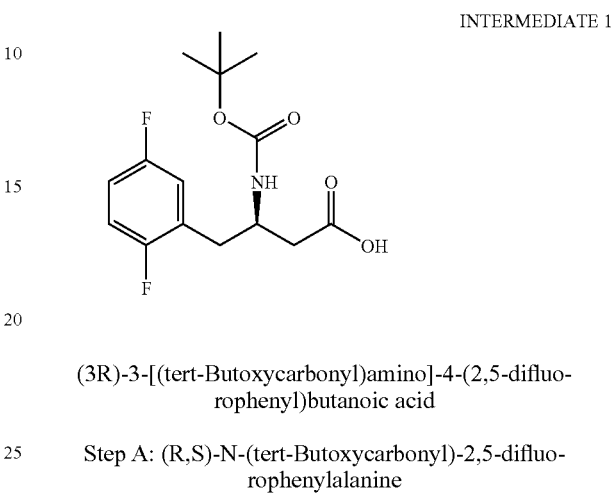

(3R)-3-[(tert-Butoxycarbonyl)amino]-4-(2,5-difluorophenyl)butanoic acid

Step A: (R,S)-N-(tert-Butoxycarbonyl)-2,5-difluorophenylalanine

To a solution of 0.5 g (2.49 mmol) of 2,5-difluoro-DL-phenylalanine in 5 mL of tert-butanol were added sequentially 1.5 mL of 2N aqueous sodium hydroxide solution and 543 mg of di-tert-butyl dicarbonate. The reaction was stirred at ambient temperature for 16 h and diluted with ethyl acetate. The organic phase was washed sequentially with 1N hydrochloric acid and brine, dried over magnesium sulfate and concentrated in vacuo. The crude material was purified by flash chromatography (silica gel, 97:2:1 dichloromethane:methanol:acetic acid) to afford 671 mg of the title compound. MS 302 (M+1).

Step B: (R,S)-3-[(tert-Butoxycarbonyl)amino]-1-diazo-4-(2,5-difluoro-phenyl)butan-2-one To a solution of 2.23 g (7.4 mmol) of (R,S)-N-(tert-butoxycarbonyl)-2,5-difluorophenylalanine in 100 mL of diethyl ether at 0° C. were added sequentially 1.37 mL (8.1 mmol) of triethylamine and 0.931 mL (7.5 mmol) of isobutyl chloroformate and the reaction was stirred at this temperature for 15 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 4:1 hexane:ethyl acetate) afforded 1.5 g of diazoketone.

$^1$H NMR (500 MHz, CDCl$_3$) δ 7.03-6.95 (m, 1H), 6.95-6.88 (m, 2H), 5.43 (bs, 1H), 5.18 (bs, 1H), 4.45 (bs, 1H), 3.19-3.12 (m, 1H), 2.97-2.80 (m, 1H), 1.38 (s, 9H).

Step C: (3R)-3-[(tert-Butoxycarbonyl)amino]-4-(2,5-difluorophenyl)butanoic acid

To a solution of 2.14 g (6.58 mmol) of (R,S)-3-[(tert-butoxycarbonyl)-amino]-1-diazo-4-(2,5-difluorophenyl)butan-2-one dissolved in 100 mL of methanol at −30° C. were added sequentially 3.3 mL (19 mmol) of diisopropylethylamine and 302 mg (1.32 mmol) of silver benzoate. The reaction was stirred for 90 min before diluting with ethyl acetate and washing sequentially with 2N hydrochloric acid, saturated aqueous sodium bicarbonate, and brine. The organic phase was dried over magnesium sulfate, concentrated in vacuo and the enantiomers were separated by preparative chiral HPLC (Chiralpak AD column, 5% ethanol in hexanes) to give 550 mg of the desired (R)-enantiomer, which eluted first. This material was dissolved in 50 mL of a mixture of tetrahydrofuran:methanol: 1N aqueous lithium hydroxide (3:1:1) and stirred at 50° C. for 4 h. The reaction was cooled, acidified with 5% dilute hydrochloric acid and extracted with ethyl acetate. The combined organic phases were washed with brine, dried over magnesium sulfate and concentrated in vacuo to give 360 mg of the title compound as a white foamy solid.

$^1$H NMR (500 MHz, CDCl$_3$) δ 7.21 (m, 1H), 6.98 (m, 2H), 6.10 (bs, 1H), 5.05 (m, 1H), 4.21 (m, 1H), 2.98 (m, 2H), 2.60 (m, 2H), 1.38 (s, 9H).

INTERMEDIATE 2

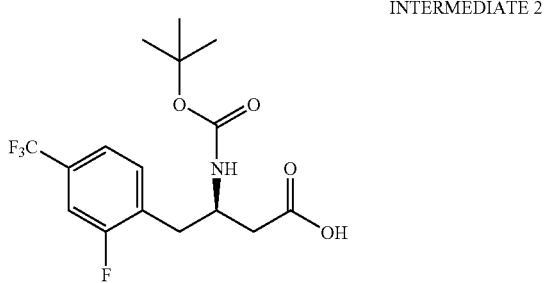

(3R)-3-[(tert-Butoxycarbonyl)amino]-4-[2-fluoro-4-(trifluoromethyl)phenyl]-butanoic acid Step A: (2R,5S)-2,5-Dihydro-3,6-dimethoxy-2-(2'-fluoro-4'-(trifluoromethyl)benzyl)-5-isopropylpyrazine To a solution of 3.32 g (18 mmol) of commercially available (2S)-2,5-dihydro-3,6-dimethoxy-2-isopropylpyrazine in 100 mL of tetrahydrofuran at −70° C. was added 12 mL (19 mmol) of a 1.6M solution of butyllithium in hexanes. After stirring at this temperature for 20 min, 5 g (19.5 mmol) of 2-fluoro-4-trifluoromethylbenzyl bromide in 20 mL of tetrahydrofuran was added and stirring was continued for 3 h before warming the reaction to ambient temperature. The reaction was quenched with water, concentrated in vacuo, and extracted with ethyl acetate. The combined organic phase was washed with brine, dried, and concentrated in vacuo. Purification by flash chromatography (silica gel, 0-5% ethyl acetate in hexanes) afforded 5.5 g of the title compound.

$^1$H NMR (500 MHz, CDCl$_3$) δ 7.33-7.25 (m, 3H), 4.35-4.31 (m, 1H), 3.75 (s, 3H), 3.65 (s, 3H), 3.60 (t, 1H, J=3.4 Hz), 3.33 (dd, 1H, J=4.6, 13.5 Hz), 3.03 (dd, 1H, J=7, 13.5 Hz), 2.25-2.15 (m, 1H), 1.0 (d, 3H, J=7 Hz), 0.66 (d, 3H, J=7 Hz).

Step B: (R)-N-(tert-Butoxycarbonyl)-2-fluoro-4-trifluoromethyl-phenylalanine methyl ester To a solution of 5.5 g (15 mmol) of (2R,5S)-2,5-dihydro-3,6-dimethoxy-2-(2'-fluoro-4'-(trifluoromethyl)benzyl)-5-isopropylpyrazine in 50 mL of a mixture of acetonitrile:dichloromethane (10:1) was added 80 mL of 1N aqueous trifluoroacetic acid. The reaction was stirred for 6 h and the organic solvents were removed in vacuo. Sodium carbonate was added until the solution was basic (>pH 8), and then the reaction was diluted with 100 mL of tetrahydrofuran and 10 g (46 mmol) of di-tert-butyl dicarbonate was added. The resulting slurry was stirred for 16 h, concentrated in vacuo, and extracted with ethyl acetate. The combined organic phase was washed with brine, dried, and concentrated in vacuo. Purification by flash chromatography (silica gel, 20% ethyl acetate in hexanes) afforded 5.1 g of the title compound.

$^1$H NMR (500 MHz, CDCl$_3$) δ 7.38-7.28 (m, 3H), 5.10 (bd, 1H), 4.65-3.98 (m, 1H), 3.76 (s, 3H), 3.32-3.25 (m, 1H), 3.13-3.05 (m, 1H), 1.40 (s, 9H).

Step C: (R)-N-(tert-Butoxycarbonyl)-2-fluoro-4-trifluoromethyl)phenyl-alanine

A solution of 5.1 g (14 mmol) of (R,S)-N-(tert-butoxycarbonyl)-2-fluoro-4-trifluoromethyl)phenylalanine methyl ester in 350 mL of a mixture of tetrahydrofuran:methanol:1N lithium hydroxide (3:1:1) was stirred at 50° C. for 4 h. The reaction was cooled, acidified with 5% hydrochloric acid and extracted with ethyl acetate. The combined organic phases were washed with brine, dried over magnesium sulfate and concentrated in vacuo to give 4.8 g of the title compound.

$^1$H NMR (500 MHz, CD$_3$OD) δ 7.45-7.38 (m, 3H), 4.44-4.40 (m, 1H), 3.38-3.33 (m, 1H), 2.98 (dd, 1H, J=9.6, 13.5 Hz), 1.44 (s, 9H).

Step D: (3R)-3-[(tert-Butoxycarbonyl)amino]-4-[2-fluoro-4-(trifluoromethyl)-phenyl]-butanoic acid To a solution of 3.4 g (9.7 mmol) of the product from Step C in 60 mL of tetrahydrofuran at 0° C. were added sequentially 2.3 mL (13 mmol) of diisopropylethylamine and 1.7 mL (13 mmol) of isobutyl chloroformate and the reaction was stirred at this temperature for 30 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 9:1 hexane:ethyl acetate) afforded 0.5 g of diazoketone. To a solution of 0.5 g (1.33 mmol) of the diazoketone dissolved in 100 mL of methanol at 0° C. were added sequentially 0.7 mL (4 mmol) of diisopropylethylamine and 32 mg (0.13 mmol) of silver benzoate. The reaction was stirred for 2 h before diluting with ethyl acetate and washing sequentially with 2N hydrochloric acid, saturated aqueous sodium bicarbonate, and brine. The organic phase was dried over magnesium sulfate, concentrated in vacuo and dissolved in 50 mL of a mixture of tetrahydrofuran:methanol:1N aqueous lithium hydroxide (3:1:1) and stirred at 50° C. for 3 h. The reaction was cooled, acidified with 5% hydrochloric acid and extracted with ethyl acetate. The combined organic phases were washed with brine, dried over magnesium sulfate and concentrated in vacuo to give 410 mg of the title compound as a white foamy solid.

$^1$H NMR (500 MHz, CD$_3$OD): δ 7.47-7.33 (m, 3H), 4.88 (bs, 1H), 4.26-3.98 (m, 1H), 3.06-3.01 (m, 1H), 2.83-2.77 (m, 1H), 2.58-2.50 (m, 2H), 1.29 (s, 9H).

INTERMEDIATE 3

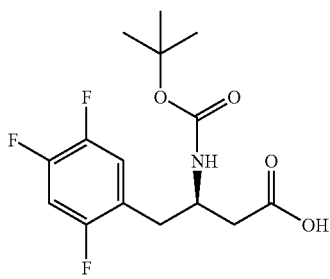

(3R)-3-[(tert-Butoxycarbonyl)amino]-4-(2,4,5-trifluorophenyl)butanoic acid

Step A: (2S,5R)-2,5-Dihydro-3,6-dimethoxy-2-isopropyl-5-(2',4',5'-trifluorobenzyl)-pyrazine The title compound (3.81 g) was prepared from 3.42 g (18.5 mmol) of (2S)-2,5-dihydro-3,6-dimethoxy-2-isopropylpyrazine and 5 g (22.3 mmol) of 2,4,5-trifluorobenzyl bromide using the procedure described for Intermediate 2, Step A.

$^1$H NMR (500 MHz, CDCl$_3$): δ 7.01 (m, 1H), 6.85 (m, 1H), 4.22 (m, 1H), 3.78 (m, 3H), 3.64 (m, 3H), 3.61 (m, 1H), 3.20 (m, 1H), 2.98 (m, 1H), 2.20 (m, 1H), 0.99 (d, 3H, J=8 Hz), 0.62 (d, 3H, J=8 Hz).

Step B: (R)-N-(tert-Butoxycarbonyl)-2,4,5-trifluorophenylalanine methyl ester To a solution of 3.81 g (11.6 mmol) of (2S,5R)-2,5-dihydro-3,6-dimethoxy-2-isopropyl-5-(2',4',5'trifluorobenzyl) pyrazine in 20 mL of acetonitrile was added 20 mL of 2N hydrochloric acid. The reaction was stirred for 72 h and concentrated in vacuo. The residue was dissolved in 30 mL of dichloromethane and 10 mL (72 mmol) of triethylamine and 9.68 g (44.8 mmol) of di-tert-butyl dicarbonate were added. The reaction was stirred for 16 h, diluted with ethyl acetate and washed sequentially with 1N hydrochloric acid and brine. The organic phase was dried over sodium sulfate, concentrated in vacuo and purified by flash chromatography (silica gel, 9:1 hexanes:ethyl acetate) to afford 2.41 g of the title compound.

$^1$H NMR (500 MHz, CDCl$_3$): δ 6.99 (m, 1H), 6.94 (m, 1H), 5.08 (m, 1H), 4.58 (m, 1H), 3.78 (m, 3H), 3.19 (m, 1H), 3.01 (m, 1H), 1.41 (s, 9H).

Step C: (R)-N-(tert-Butoxycarbonyl)-2,4,5-trifluorophenylalanine

The title compound (2.01 g) was prepared from 2.41 g (7.5 mol) of (R)-N-(tert-butoxycarbonyl)-2,4,5-trifluorophenylalanine methyl ester using the procedure described for Intermediate 2, Step C.

LC-MS 220.9 (M+1-BOC).

Step D: (3R)-3-[(tert-Butoxycarbonyl)amino]-4-(2,4,5-trifluorophenyl)-butanoic acid To a solution of 0.37 g (1.16 mmol) of (R)-N-(1,1-dimethylethoxy-carbonyl)-2,4,5-trifluorophenylalanine in 10 mL of diethyl ether at −20° C. were added sequentially 0.193 mL (1.3 mmol) of triethylamine and 0.18 mL (1.3 mmol) of isobutyl chloroformate, and the reaction was stirred at this temperature for 15 min. A cooled ethereal solution of diazomethane was then added until the yellow color persisted and stirring was continued for a further 1 h. The excess diazomethane was quenched by dropwise addition of acetic acid, and the reaction was diluted with ethyl acetate and washed sequentially with saturated aqueous sodium bicarbonate solution and brine, dried over magnesium sulfate and concentrated in vacuo. Purification by flash chromatography (silica gel, 3:1 hexane:ethyl acetate) afforded 0.36 g of diazoketone. To a solution of 0.35 g (1.15 mmol) of the diazoketone dissolved in 12 mL of 1,4-dioxane: water (5:1) was added 26 mg (0.113 mmol) of silver benzoate. The resultant solution was sonicated for 2 h before diluting with ethyl acetate and washing sequentially with 1N hydrochloric acid and brine, drying over magnesium sulfate and concentrating in vacuo. Purification by flash chromatography (silica gel, 97:2:1 dichloromethane:methanol:acetic acid) afforded 401 mg of the title compound.

$^1$H NMR (500 MHz, CDCl$_3$) δ 7.06 (m, 1H), 6.95 (m, 1H), 5.06 (bs, 1H), 4.18 (m, 1H), 2.98 (m, 2H), 2.61 (m, 2H), 1.39 (s, 9H).

INTERMEDIATE 4

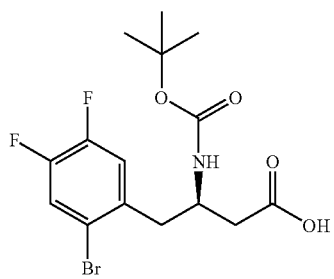

(3R)-4-(2-Bromo-4,5-difluorophenyl)-3-[(tert-butoxycarbonyl)amino]-butanoic acid To a solution of 2.4 g (10 mmol) of 2-bromo-4,5-difluorobenzoic acid [prepared according to the procedure of Braish et al., *Syn. Comm.*, 3067-3074 (1992)] in 75 mL of tetrahydrofuran was added 2.43 g (15 mmol) of carbonyldiimidazole. The solution was heated under reflux for 3.5 h, cooled to ambient temperature and 0.38 g (10 mmol) of sodium borohydride in 15 mL of water was added. The reaction was stirred for 10 min and partitioned between ethyl acetate and 10% aqueous sodium bicarbonate solution. The organic layer was washed twice with warm water, brine, dried over magnesium sulfate, and concentrated in vacuo. Purification by flash chromatography (silica gel, 4:1 hexane:ethyl acetate) afforded 1.9 g of 2-bromo-4,5-difluorobenzyl alcohol. To a solution of 1.9 g (8.4 mmol) of 2-bromo-4,5-difluorobenzyl alcohol in 30 mL of dichloromethane at 0° C. was added 3.4 g (10 mmol) of carbon tetrabromide and 2.7 g (10 mmol) of triphenylphosphine. The reaction was stirred for 2 h at this temperature, the solvent was removed in vacuo and the residue stirred with 100 mL of diethyl ether. The solution was filtered, concentrated in vacuo, and purified by flash chromatography (silica gel, 20:1 hexane:ethyl acetate) to afford 2.9 g of 2-bromo-4,5-difluorobenzyl bromide contaminated with carbon tetrabromide which was used without further purification. Using the procedures outlined for the preparation of Intermediates 2-4, the benzyl bromide derivative was converted to the title compound.

LC-MS 394 and 396 (M+1).

Essentially following the procedures outlined for the preparation of Intermediates 1-4, the Intermediates in Table 1 were prepared.

TABLE 1

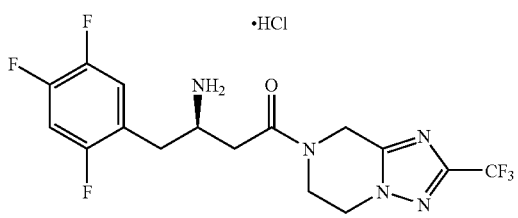

| Intermediate | R³ | Selected ¹H NMR data (CD$_3$OD) |
|---|---|---|
| 5 | 2-F,4-Cl,5-F | 7.11 (dd, 1 H, J=8.9, 6.4 Hz), 7.03 (dd, 1 H, J=9.0, 6.6) |
| 6 | 2-F,5-Cl | 7.27 (dd, 1 H, J=6.4, 2.5 Hz), 7.21 (m. 1 H), 7.03 (t, 1 H, J=9.2 Hz) |
| 7 | 2-Me,5-Cl | 7.16 (d, 1 H, J=1.8 Hz), 7.11-7.07 (m, 2 H), 2.34 (s, 3 H) |
| 8 | 2-Cl,5-Cl | 7.34 (d, 1 H, J=9.0), 7.33 (d, 1 H, J=2.1 Hz), 7.21 (dd, 1 H, J=8.5, 2.5 Hz) |
| 9 | 2-F,3-Cl,6-F | 7.35 (td, 1 H, J=8.5, 5.8 Hz), 6.95 (t, 1 H, J=8.5 Hz) |
| 10 | 3-Cl,4-F | 7.33 (d, 1 H, J=6.9 Hz), 7.19-7.11 (m, 2 H) |
| 11 | 2-F,3-F,6-F | 7.18-7.12 (m, 1 H), 6.91 (m, 1 H) |
| 12 | 2-F,4-F,6-F | 6.81 (t, 2 H, J=8.4 Hz) |
| 13 | 2-OCH$_2$Ph,5-F | 7.49 (d, 2 H, J=7.6 Hz), 7.38 (t, 2 H, J=7.3 Hz), 7.30 (t, 1 H, J=7.3 Hz), 6.96-6.89 (m, 3 H), 5.11 (d, 1 H, J=11.7 Hz), 5.08 (d, 1 H, J=11.9 Hz) |

EXAMPLE 1

7-[(3R)-3-Amino-4-(2,4,5-trifluorophenyl)butanoyl]-2-(trifluoromethyl)-5,6,7,8-tetrahydro[1,2,4]triazolo[1,5-α]pyrazine, hydrochloride Step A: 2,2,2-Trifluoro-N-pyrazin-2-ylacetamide To a slightly heterogeneous solution of aminopyrazine (22.74 g, 239 mmol) and triethylamine (36.66 mL, 263 mmol) in dichloromethane (400 mL) was added trifluoroacetic anhydride (50.20 g, 239 mmol) dropwise at 0° C. The solution was stirred at 0° C. for 1 h and at ambient temperature for 2 h. Filtration of the resultant white precipitate followed by washing with dichloromethane afforded the title compound as a white solid.

¹H NMR (500 MHz, CD$_3$OD): δ 8.44-8.46 (m, 2H), 9.33 (d, 1H, J=1.4 Hz); LC/MS 192 (M+1).

Step B: 2,2,2-Trifluoro-N'-hydroxy-N-pyrazin-2-ylethanimidamide

To a suspension of 2,2,2-trifluoro-N-pyrazin-2-ylacetamide (14.56 g, 76.26 mmol, from Step A) in dichloroethane (325 mL) was added phosphorous pentachloride (421.73 g, 99.13 mmol) portionwise. The mixture was refluxed for 5 h. After evaporation of dichloroethane, the residue was suspended in tetrahydrofuran (325 mL). To the above mixture was added 50% aqueous hydroxylamine (20 mL) dropwise. After stirring at ambient temperature for 2 h, the mixture was partitioned between ethyl acetate and aqueous sodium bicarbonate. The aqueous layer was extracted three times with ethyl acetate. The combined organic layers were washed with brine and dried over anhydrous magnesium sulfate. Concentration gave the title compound as a yellow solid.

¹H-NMR (500 MHz, CD$_3$OD): δ 8.04 (m, 2H), 8.17 (s, 1H). LC/MS 207 (M+1).

Step C: 2-(Trifluoromethyl)[1,2,4]triazolo[1,5-α] pyrazine

A mixture of 2,2,2-trifluoro-N'-hydroxy-N-pyrazin-2-ylethanimidamide (10.5 g, 50.97 mmol, from Step B) and polyphosphoric acid (80 mL) was heated to 150° C. with stirring for 18 h. The solution was added to ice and neutralized by addition of ammonium hydroxide. The dark aqueous solution was extracted three times with ethyl acetate, washed with brine, and dried over anhydrous magnesium sulfate. Concentration followed by flash chromatography (50% then 100% ethyl acetate/hexane) afforded the title compound as a yellow solid.

¹H-NMR (500 MHz, CDCl$_3$): δ 8.42 (d, 1H, J=4.6 Hz), 8.67 (dd, 1H, J=1.4 and 4.6 Hz), 9.47 (d, 1H, J=1.4 Hz). LC/MS 189 (M+1).

Step D: 2-(Trifluoromethyl)-5,6,7,8-tetrahydro[1,2,4]triazolo[1,5-α]pyrazine 2-(Trifluoromethyl)-[1,2,4]triazolo[1,5-α]pyrazine (340 mg, 1.81 mmol, from Step C) was hydrogenated under atmospheric hydrogen with 10% palladium on carbon (60 mg) as a catalyst in ethanol (10 mL) at ambient temperature for 18 h. Filtration through Celite followed by concentration gave a dark colored oil. Flash chromatography (100% ethyl acetate, then 10% methanol/dichloromethane) gave the title compound as a white solid.

¹H-NMR (500 MHz, CDCl$_3$): δ 1.80 (br, 1H), 3.40 (t, 2H, J=5.5 Hz), 4.22-4.26 (m, 4H); LC/MS 193 (M+1).

Step E: 7-[(3R)-3-[(tert-Butoxycarbonyl)amino]-4-(2,4,5-trifluorophenyl)butanoyl]-2-(trifluoromethyl)-5,6,7,8-tetrahydro[1,2,4]triazolo[1,5-α]pyrazine To a solution of 2-(trifluoromethyl)-5,6,7,8-tetrahydro[1,2,4]triazolo[1,5-α]pyrazine (28.8 mg, 0.15 mmol, from Step D) and (3R)-3-[(tert-butoxycarbonyl)amino]-4-(2,4,5-trifluorophenyl)butanoic acid (Intermediate 3, 50.0 mg, 0.15 mmol) in DMF (3 mL) was added hydroxybenzotriazole (HOBT, 26.1 mg, 0.19 mmol) at 0° C. The reaction was stirred at 0° C. for 5 min, then 1-(3-dimethylaminopropyl)-3-ethyl-carbodiimide hydrochloride (EDC, 37.0 mg, 0.19 mmol) was added. After removal of the ice-bath, the reaction was allowed to stir at ambient temperature for 16 h. After removal of the DMF by evaporation, the residue was partitioned between ethyl acetate and aqueous sodium bicarbonate. The aqueous layer was extracted three times with ethyl acetate. The combined organic layers were washed with brine and dried over magnesium sulfate. Concentration followed by preparative TLC (10% methanol/dichloromethane) gave the title compound as a foamy solid.

$^1$H NMR (500 MHz, CDCl$_3$): δ 1.38 (s, 9H), 2.60-3.00 (m, 4H), 3.95-4.40 (m, 5H), 4.84 (s, 1H), 4.95-5.02 (m, 1H), 5.30 (br s, 1H), 6.85-6.95 (m, 1H), 7.05-7.13 (m, 1H); LC/MS 408 (M+1-BOC).

Step F: 7-[(3R)-3-Amino-4-(2,4,5-trifluorophenyl) butanoyl]-2-(trifluoromethyl)-5,6,7,8-tetrahydro[1,2,4triazolo[1,5-α]pyrazine, hydrochloride To 7-[(3R)-3-[(tert-butoxycarbonyl)amino]-4-(2,4,5-trifluorophenyl) butanoyl]-2-(trifluoromethyl)-5,6,7,8-tetrahydro[1,2,4]triazolo[1,5-α]pyrazine (63.1 mg, 0.12 mmol, from Step E) was added 3 mL of methanol saturated with hydrogen chloride at 0° C. The reaction was stirred at ambient temperature for 45 min. Concentration gave the title compound as a white solid.

$^1$H NMR (500 MHz, CD$_3$OD): δ 2.75-3.15 (m, 4H), 3.85-3.95 (m, 1H), 4.00-4.40 (m, 4H), 4.90-5.00 (m, 2H), 7.18-7.25 (m, 1H), 7.32-7.42 (m, 10H). ESI-MS 408 (M+1).

EXAMPLE 2

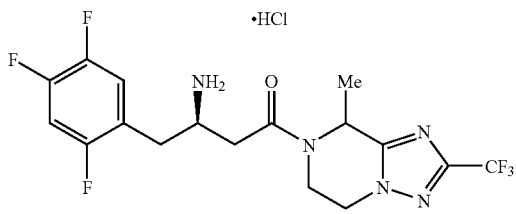

7-[(3R)-3-Amino-4-(2,4,5-trifluorophenyl)butanoyl]-8-methyl-2-(trifluoromethyl)-5,6,7,8-tetrahydro[1,2,4]triazolo[1,5-α]pyrazine, hydrochloride Step A: 7-N-(tert-Butoxycarbonyl)-2-(trifluoromethyl)-5,6,7,8-tetrahydro[1,2,4]triazolo[1,5-α]pyrazine To a solution of 2-(trifluoromethyl)-5,6,7,8-tetrahydro[1,2,4]triazolo[1,5-α]pyrazine (3.68 g, 19.18 mmol, Step D, Example 1) in 70 mL of dichloromethane was added di-tert-butyl dicarbonate (4.60 g, 21.10 mmol) and 3.34 mL (19.18 mmol) of diisopropylethylamine. The reaction mixture was allowed to stir at ambient temperature overnight. After evaporation of dichloromethane, the residue was partitioned between saturated aqueous sodium bicarbonate solution and ethyl acetate. The aqueous phase was extracted with three portions of ethyl acetate, and the combined organic phases were washed with brine, dried over magnesium sulfate, and concentrated. Flash chromatography (silica gel, 10% followed by 20% ethyl acetate/hexane) yielded the title compound as a clear oil.

$^1$H-NMR (500 MHz, CDCl$_3$): δ 1.51 (s, 9H), 3.99 (t, 2H, J=5.3 Hz), 4.28 (t, 2H, J=5.5 Hz), 4.81 (s, 2H); LC/MS 237 (M+1-t-Bu).

Step B: 7-N-(tert-Butoxycarbonyl)-8-methyl-2-(trifluoromethyl)-5,6,7,8-tetrahydro[1,2,4]triazolo[1,5-α] pyrazine To a solution of 7-N-(tert-butoxycarbonyl)-2-(trifluoromethyl)-5,6,7,8-tetrahydro[1,2,4]triazolo[1,5-α]pyrazine (1.85 g, 6.35 mmol) in 25 mL of toluene at –78° C. was added N,N,N,N-tetramethylethylenediamine (1.01 mL, 6.67 mmol) followed by n-butyllithium (4.17 mL of a 1.6 M solution in hexanes, 6.67 mmol). The mixture was stirred at –78° C. for 10 min and then iodomethane (0.415 mL, 6.67 mmol) was added dropwise. The mixture was allowed to stir at –78° C. for 10 min, and then it was warmed to ambient temperature. The reaction was quenched with aqueous ammonium chloride and the aqueous layer was extracted three times with ethyl acetate. The combined organic layers were washed with brine, dried over magnesium sulfate, and concentrated. Purification by flash chromatography (silica gel, 10% ethyl acetate/hexane) yielded the title compound.

$^1$H-NMR (500 MHz, CDCl$_3$): δ 1.55 (s, 9H), 1.61 (d, 3H, J=6.9 Hz), 3.40 (br 1H), 4.22-4.27 (m, 1H), 4.30-4.35 (m, 1H), 4.62 (br 1H), 5.50 (br 1H); LC/MS 251 (M+1-t-Bu).

Step C: 8-Methyl-2-(trifluoromethyl)-5,6,7,8-tetrahydro[1,2,4]triazolo[1,5-α]pyrazine, hydrochloride To a solution of 7-N-(tert-butoxycarbonyl)-8-methyl-2-(trifluoromethyl)-5,6,7,8-tetrahydro[1,2,4]triazolo[1,5-α] pyrazine (2.40 g, 7.83 mmol) in 40 mL of methanol was added 50 mL of methanol saturated with hydrogen chloride. The reaction was stirred at ambient temperature for 1 h. Concentration in vacuo gave the title compound as an off-white solid.

$^1$H NMR (500 MHz, CD$_3$OD): δ 1.82 (d, 3H, J=6.8 Hz), 3.82-3.88 (m, 1H), 3.98-4.05 (m, 1H), 4.53-4.65 (m, 2H), 4.95 (q, 1H, J=6.9 Hz); LC/MS 207 (M+1).

Step D: 7-[(3R)-3-[(tert-Butoxycarbonyl)amino]-4-(2,4,5-trifluorophenyl)butanoyl]-8-methyl-2-(trifluoromethyl)-5,6,7,8-tetrahydro[1,5-α]pyrazine To a solution of 8-methyl-2-(trifluoromethyl)-5,6,7,8-tetrahydro[1,2,4]triazolo[1,5-α]pyrazine, hydrochloride (103 mg, 0.50 mmol, from Step C), (3R)-3-[(tert-butoxycarbonyl) amino]-4-(2,4,5-trifluorophenyl)butanoic acid (Intermediate 3, 175 mg, 0.53 mmol), and N,N-diisopropylethylamine (0.096 mL, 0.55 mmol) in DMF (1.5 mL) was added 1-hydroxy-7-azabenzotriazole (HOAT) (81.7, 0.60 mmol) followed by O-(7-azabenzotriazol-1-yl)-N,N,N',N'-tetramethyluronium hexafluorophosphate (HATU) (228 mg, 0.60 mmol). The solution was stirred at ambient temperature for 24 h. After removal of the DMF by evaporation, the residue was partitioned between ethyl acetate and aqueous sodium bicarbonate. The aqueous layer was extracted three times with ethyl acetate. The combined organic layers were washed with brine, dried over anhydrous magnesium sulfate, and concentrated. Purification by flash chromatography (25% ethyl acetate/hexane) gave the title compound as a mixture of diastereomers. The diastereomers were separated by HPLC (Gilson, OD Chiralcel column, 7% ethyl acetate/hexane). Faster eluting diastereomer: $^1$H NMR (500 MHz, CDCl$_3$) δ 1.38, (s, 9H), 1.50-1.80 (m, 3H), 2.45-3.10 (m, 4H), 3.20-3.30 (m, 0.5H), 3.66-3.80 (m, 0.5H), 4.05-4.45 (m, 3.5H), 5.10-5.20 (m, 0.5H), 5.20-5.40 (m, 1.5H), 5.90-6.00 (m, 0.5H), 6.80-7.00 (m, 1H), 7.02-7.18 (m, 1H); LC/MS 422 (M+1-Boc; Slower eluting diastereomer: $^1$H NMR (500 MHz, CDCl$_3$) δ 1.39, (s, 9H), 1.50-1.75 (m, 3H), 2.60-3.05 (m, 4H), 3.20-3.30 (m, 0.5H), 3.65-3.75 (m, 0.5H), 4.00-4.40 (m, 3.5H), 5.10-5.18 (m, 0.5H), 5.18-5.42 (m, 1.5H), 5.90-5.99 (m, 0.5H), 6.85-6.95 (m, 1H), 6.95-7.15 (m, 1H); LC/MS 422 (M+1-BOC).

Step E: 7-[(3R)-3-Amino-4-(2,4,5-trifluorophenyl) butanoyl]-8-methyl-2-(trifluoromethyl)-5,6,7,8-tetrahydro[1,2,4]triazolo[1,5-α]pyrazine, hydrochloride To a solution of 46.4 mg of the slower eluting diastereomer of 7-[(3R)-3-[(tert-butoxycarbonyl)amino]-4-(2,4,5-trifluorophenyl)butanoyl]-8-methyl-2-(trifluoromethyl)-5,6,7,8-tetrahydro[1,2,4]triazolo[1,5-α]pyrazine from Step D in 15 mL of methanol was added 20 mL of methanol saturated with hydrogen chloride. After 30 min, the reaction was concentrated in vacuo to give the title compound as a white solid.

In a separate experiment, to a solution of 46.8 mg of the faster eluting diastereomer in 5 mL of methanol was added 6 mL of methanol saturated with hydrogen chloride. The reaction was stirred at ambient temperature for 30 min. Concentration gave the product as a white solid.

Compound from the faster eluting diastereomer: $^1$H NMR (500 MHz, CD$_3$OD) δ 1.50-1.75 (m, 3H), 2.80-3.15 (m, 4H), 3.39-3.46 (m, 0.3H), 3.80-3.95 (m, 1.7H), 4.19 (dt, 0.3H, J=4.2, 12.6 Hz), 4.23-4.40 (m, 2.4H), 5.00 (dd, 0.3H, J=4.3, 14.2 Hz), 5.34 (q, 0.3H, J=7.1 Hz), 5.82 (q, 0.7H, J=6.9 Hz), 7.20-7.30 (m, 1H), 7.35-7.44 (m, 1H); LC/MS 422 (M+1); Compound from the slower eluting diastereomer: $^1$H NMR (500 MHz, CD$_3$OD) δ1.54 (d, 2.1H, J=6.8 Hz), 1.66 (d, 0.9H, J=6.9 Hz), 2.70-3.16 (m, 4H), 3.40-3.46 (m, 0.3H), 3.75-3.98 (m, 1.7H), 4.13 (dt, 0.3H, J=4.1, 11.9 Hz), 4.25-4.42 (m, 2.4H), 5.00 (dd, 0.3H, J=4.1, 14.0 Hz), 5.33 (q, 0.3H, J=7.1 Hz), 5.84 (q, 0.7H, J=6.9 Hz), 7.20-7.30 (m, 1H), 7.35-7.45 (m, 1H); LC/MS 422 (M+1).

EXAMPLE 3

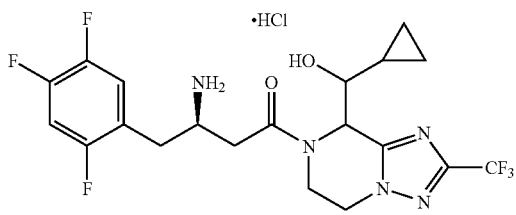

[7-[(3R)-3-Amino-4-(2,4,5-trifluorophenyl)butanoyl]-2-(trifluoromethyl)-5,6,7,8-tetrahydro[1,2,4]triazolo[1,5-α]pyrazin-8-yl](cyclopropyl)methanol, hydrochloride Step A: [7-N-(tert-Butoxycarbonyl)-2-(trifluoromethyl)-5,6,7,8-tetrahydro[1,2,4]triazolo[1,5-α] pyrazin-8-yl](cyclopropyl)methanol To a solution of 1.86 g (6.38 mmol) of 7-N-(tert-butoxycarbonyl)-2-(trifluoromethyl)-5,6,7,8-tetrahydro[1,2,4]triazolo[1,5-α]pyrazine (Ex. 2, Step A) in 20 mL of toluene at −78° C. was added 5.88 mL (7.65 mmol, 1.3 M solution in cyclohexane) of sec-butyllithium. The reaction mixture was stirred at −78° C. for 20 min, then 0.524 mL (7.01 mmol) of cyclopropanecarboxaldehyde was added dropwise. The reaction mixture was stirred at −78° C. for 10 min. The −78° C. bath was removed and the mixture was allowed to stir at ambient temperature for 1 h. The reaction was quenched by the addition of saturated aqueous ammonium chloride solution and extracted with three portions of ethyl acetate. The combined organic phases were washed with brine, dried over magnesium sulfate, and concentrated to give 2.24 g of crude material. Purification by flash chromatography (silica gel, 7 to 10% ethyl acetate/hexane) gave the title compound as a mixture of 4 diastereomers. LC/MS 363 (M+1).

Step B: [2-(Trifluoromethyl)-5,6,7,8-tetrahydro[1,2, 4]triazolo[1,5-α]pyrazin-8-yl](cyclopropyl)methanol, hydrochloride The BOC protecting group was removed from a 400 mg portion of 7-N-(tert-butoxycarbonyl)-2-(trifluoromethyl)-5,6,7,8-tetrahydro[1,2,4]triazolo[1,5-α]pyrazin-8-yl](cyclopropyl)methanol essentially following the procedure outlined in Example 2, Step C to provide the title compound.
LC/MS 245 (M+1-H$_2$O).

Step C: [7-[(3R)-3-[(tert-Butoxycarbonyl)amino]-4-(2,4,5-trifluorophenyl)butanoyl]-2-(trifluoromethyl)-5,6,7,8-tetrahydro[1,2,4]triazolo[1,5-α]pyrazin-8-yl](cyclopropyl)methanol A 160 mg portion of [2-(trifluoromethyl)-5,6,7,8-tetrahydro[1,2,4]triazolo[1,5-α]pyrazin-8-yl](cyclopropyl)methanol hydrochloride was coupled to (3R)-3-[(tert-butoxycarbonyl)amino]-4-(2,4,5-trifluorophenyl)butanoic acid essentially following the procedure outlined in Example 2, Step D. Purification by preparative TCL (silica gel, 10% methanol/dichloromethane) gave 176 mg of the product as a mixture of diastereomers. HPLC (OD chiralcel column, 6% ethanol/hexane) separated the first and last eluting diastereomers. The middle fractions containing two diastereomers were further subjected to HPLC (OD chiralcel column, 3% ethanol/hexane) to provide the second and the third eluting diastereomers.
LC/MS 504 (M+1-tBu-H$_2$O).

Step D: [7-[(3R)-3-Amino-4-(2,4,5-trifluorophenyl) butanoyl]-2-(trifluoromethyl)-5,6,7,8-tetrahydro[1,2, 4]triazolo[1,5-α]pyrazin-8-yl](cyclopropyl)methanol hydrochloride The BOC protecting group was removed from a 12 mg portion of [7-[(3R)-3-[(tert-butoxycarbonyl)amino]-4-(2,4, 5-trifluorophenyl)butanoyl]-2-(trifluoromethyl)-5,6,7,8-tetrahydro[1,2,4]triazolo[1,5-α]pyrazin-8-yl](cyclopropyl) methanol (second eluting diastereomer) essentially following the procedure outlined in Example 2, Step E to provide the title compound as a single diastereomer of unknown configuration. LC/MS 478 (M+1). The other isomers were deprotected in a similar manner.

EXAMPLE 4

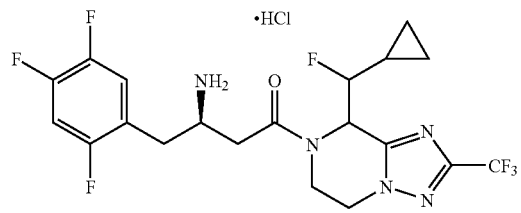

7-[(3R)-3-Amino-4-(2,4,5-trifluorophenyl)butanoyl]-8-[cyclopropyl(fluoro)methyl]-2-(trifluoromethyl)-5,6,7,8-tetrahydro[1,2,4]triazolo[1 5-α]pyrazine, hydrochloride Step A: 7-N-(tert-Butoxycarbonyl)-8-[cyclopropyl(fluoro)methyl]-2-(trifluoromethyl)-5,6,7,8-tetrahydro[1,2,4]triazolo[1,5-α]pyrazine A solution of 200 mg (0.55 mmol) of [7-N-(tert-butoxycarbonyl)-2-(trifluoromethyl)-5,6,7,8-tetrahydro[1,2,4]triazolo[1,5-α]pyrazin-8-yl](cyclopropyl)methanol (prepared as outlined in Example 3, Step A) in 3.5 mL of dichloromethane was cooled to −78° C. and 0.406 mL (3.31 mmol) of (diethylamino)sulfur trifluoride (DAST) was added. The reaction mixture was stirred at −78° C. for 1 h, then warmed to ambient temperature and stirred overnight. The reaction mixture was partitioned between saturated aqueous sodium bicarbonate solution and dichloromethane. The aqueous phase was extracted with three portions of dichloromethane. The combined organic phases were washed with brine, dried over magnesium sulfate, and concentrated. Purification by HPLC (Gilson, YMC C-18, 10 to 90% acetonitrile/water gradient) gave the title compound.
LC/MS 289 (M+1-tBu-HF).

Step B: 8-[Cyclopropyl(fluoro)methyl]-2-(trifluoromethyl)-5,6,7,8-tetrahydro[1,2,4]triazolo[1,5-α]pyrazine, hydrochloride The BOC protecting group was removed from a 100 mg portion of 7-N-(tert-butoxycarbonyl)-8-[cyclopropyl(fluoro)methyl]-2-(trifluoromethyl)-5,6,7,8-tetrahydro[1,2,4]triazolo[1,5-α]pyrazine essentially following the procedure outlined in Example 2, Step C to provide the title compound. LC/MS 265 (M+1).

Step C: 7-[(3R)-3-[(tert-Butoxycarbonyl)amino]-4-(2,4,5-trifluorophenyl)butanoyl]-8-[cyclopropyl(fluoro)methyl]-2-(trifluoromethyl)-5,6,7,8-tetrahydro[1,2,4]triazolo[1,5-α]pyrazine A 90 mg portion of 8-[cyclopropyl(fluoro)methyl]-2-(trifluoromethyl)-5,6,7,8-tetrahydro[1,2,4]triazolo[1,5-α]pyrazine hydrochloride was coupled to (3R)-3-[(tert-butoxycarbonyl)amino]-4-(2,4,5-trifluorophenyl)butanoic acid essentially following the procedure outlined in Example 2, Step D with the exception that the reaction mixture was stirred for 3 days. Purification by HPLC (OD chiralcel column, 7% ethanol/hexane) gave 1.8 mg of the first eluting diastereomer, 22.7 mg of the second, 7.4 mg of the third, and 24.4 mg of the fourth eluting diastereomer. LC/MS 480 (M+1-BOC).

Step D: 7-[(3R)-3-Amino-4-(2,4,5-trifluorophenyl)butanoyl]-8-[cyclopropyl(fluoro)methyl]-2-(trifluoromethyl)-5,6,7,8-tetrahydro[1,2,4]triazolo[1,5-α]pyrazine hydrochloride The BOC protecting group was removed from a 24 mg portion of 7-[(3R)-3-[(tert-butoxycarbonyl)amino]-4-(2,4,5-trifluorophenyl)butanoyl]-8-[cyclopropyl(fluoro)methyl]-2-(trifluoromethyl)-5,6,7,8-tetrahydro[1,2,4]triazolo[1,5-α]pyrazine (fourth eluting diastereomer from Step C) essentially following the procedure outlined in Example 2, Step E to provide the title compound as a single diastereomer of unknown configuration. LC/MS 480 (M+1). The other isomers were deprotected in a similar manner.

EXAMPLE 5

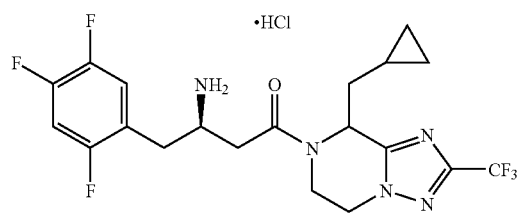

7-[(3R)-3-Amino-4-(2,4,5-trifluorophenyl)butanoyl]-8-(cyclopropylmethyl)-2-(trifluoromethyl)-5,6,7,8-tetrahydro[1,2,4]triazolo[1,5-α]pyrazine, hydrochloride Step A: tert-Butyl 8-(cyclopropylmethylene)-2-(trifluoromethyl)-5,6-dihydro[1,2,4]triazolo[1,5-α]pyrazine-7(8H)-carboxylate A solution of 100 mg (0.28 mmol) of [7-N-(tert-butoxycarbonyl)-2-(trifluoromethyl)-5,6,7,8-tetrahydro [1,2,4]triazolo[1,5-α]pyrazin-8-yl](cyclopropyl)methanol (prepared as outlined in Example 3, Step A), 52.4 mg (0.294 mmol) of 1,1-thiocarbonyldiimidazole, and 3.4 mg (0.028 mmol) of 4-(dimethylamino)pyridine in 2.0 mL of dichloroethane was stirred at reflux temperature for 17 h. The reaction mixture was cooled to ambient temperature and concentrated in vacuo. The residue was partitioned between saturated aqueous sodium bicarbonate solution and ethyl acetate. The aqueous phase was extracted with three portions of ethyl acetate. The combined organics were washed with brine, dried over magnesium sulfate and concentrated. Purification by preparative TLC (silica gel) gave the title compound as a clear semi-solid.
LC/MS 289 (M+1-tBu).

Step B: 7-N-(tert-Butoxycarbonyl)-8-(cyclopropylmethyl)-2-(trifluoromethyl)-5,6,7,8-tetrahydro[1,2,4]triazolo[1,5-α]pyrazine A mixture of 50 mg (0.15 mmol) of tert-butyl 8-(cyclopropylmethylene)-2-(trifluoromethyl)-5,6-dihydro[1,2,4]triazolo[1,5-α]pyrazine-7(8H)-carboxylate and 25 mg of 10% palladium on carbon in 0.5 mL of ethanol was stirred under an atmosphere of hydrogen overnight. The mixture was filtered and the filtrate concentrated to give the title compound.
LC/MS 291 (M+1-tBu).

Step C: 8-(Cyclopropylmethyl)-2-(trifluoromethyl)-5,6,7,8-tetrahydro[1,2,4]triazolo[1,5-α]pyrazine hydrochloride The BOC protecting group was removed from a 42 mg portion of 7-N-(tert-butoxycarbonyl)-8-(cyclopropylmethyl)-2-(trifluoromethyl)-5,6,7,8-tetrahydro[1,2,4]triazolo[1,5-α]pyrazine essentially following the procedure outlined in Example 2, Step C to provide the title compound.
LC/MS 247 (M+1).

Step D: 7-[(3R)-3-[(tert-Butoxycarbonyl)amino]-4-(2,4,5-trifluorophenyl)butanoyl]-8-(cyclopropylmethyl)-2-(trifluoromethyl)-5,6,7,8-tetrahydro[1,2,4]triazolo[1,5-α]pyrazine A 35 mg portion of 8-(cyclopropylmethyl)-2-(trifluoromethyl)-5,6,7,8-tetrahydro[1,2,4]triazolo[1,5-α]pyrazine hydrochloride was coupled to (3R)-3-[(tert-butoxycarbonyl)amino]-4-(2,4,5-trifluorophenyl)butanoic acid essentially following the procedure outlined in Example 2, Step D, with the following exception. The reaction mixture was stirred at ambient temperature for 24 h and then concentrated. The residue was purified by preparative TLC (silica gel, 10% methanol/dichloromethane) to provide 54 mg of the title compound as a mixture of diastereomers. The diastereomers were separated by HPLC (OD chiralcel column, 7% ethanol/hexane) to give the faster eluting diastereomer and the slower eluting diastereomer.
LC/MS 462 (M+1-BOC).

Step E: 7-[(3R)-3-Amino-4-(2,4,5-trifluorophenyl)butanoyl]-8-(cyclopropylmethyl)-2-(trifluoromethyl)-5,6,7,8-tetrahydro[1,2,4]triazolo[1,5-α]pyrazine hydrochloride The BOC protecting group was removed from a 12 mg portion of 7-[(3R)-3-[(tert-butoxycarbonyl)amino]-4-(2,4,5-trifluorophenyl)butanoyl]-8-(cyclopropylmethyl)-2-(trifluoromethyl)-5,6,7,8-tetrahydro[1,2,4]triazolo[1,5-α]pyrazine (slower eluting diastereomer from Step C) essentially following the procedure outlined in Example 2, Step E to provide the title compound as a single diastereomer of unknown configuration. LC/MS 462 (M+1). The other isomer was deprotected in a similar manner.

EXAMPLE 6

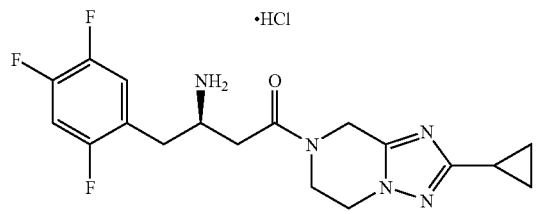

7-[(3R)-3-Amino-4-(2,4,5-trifluorophenyl)butanoyl]-2-cyclopropyl-5,6,7,8-tetrahydro[1,2,4]triazolo[1 5-α]pyrazine, hydrochloride

Step A: N-Pyrazin-2-ylcyclopropanecarboxamide

To a solution of 10 g (105 mmol) of 2-aminopyrazine in 100 mL of pyridine was added dropwise a solution of 10.99 g (9.56 mL, 105 mmol) of cyclopropanecarbonyl chloride in 100 mL of dichloromethane. The resultant yellow solution was stirred at ambient temperature for 2 h. The reaction mixture was concentrated in vacuo. The residue was dissolved in ethyl acetate and a small amount of water and washed sequentially with 1 M aqueous cuprous sulfate solution and water. The water layer was extracted with three portions of ethyl acetate. The combined organic phases were washed with brine, dried over magnesium sulfate, and concentrated. Purification by flash chromatography (silica gel, eluting sequentially with 50%, 80% and 100% ethyl acetate/hexane) gave the title compound.
LC/MS 164 (M+1).

Step B: 1-Amino-2-[(cyclopropylcarbonyl)amino]pyrazin-1-ium 2,4,6-trimethylbenzenesulfonate To a solution of 1.0 g (6.13 mmol) of N-pyrazin-2-ylcyclopropanecarboxamide in 10 mL of dichloromethane at 0° C. was added a solution of 1.58 g (7.36 mmol) of O-mesitylenesulfonylhydroxylamine, prepared from mesitylenesulfonyl chloride using a procedure analogous to that described in the literature (Y. Tamura et al., *J. Org. Chem.*, 38: 1239 (1973)). The reaction mixture was allowed to stir at ambient temperature for 1.5 h. The resultant thick yellow mixture was concentrated in vacuo to give the title compound as a yellow solid.
LC/MS 179 (M).

Step C: 2-Cyclopropyl[1,2,4]triazolo[1,5-α]pyrazine

1-Amino-2-[(cyclopropylcarbonyl)amino]pyrazin-1-ium 2,4,6-trimethylbenzene-sulfonate (2.6 g) was cyclized using polyphosphoric acid, essentially following the procedure outlined in Example 1, Step C, except that the mixture was heated at 130° C. Purification by HPLC (Gilson, YMC C-18 column, 90 to 10% water/acetonitrile gradient) gave the title compound.
LC/MS 161 (M+1).

Step D: 2-Cyclopropyl-5,6,7,8-tetrahydro[1,2,4]triazolo[1,5-α]pyrazine hydrochloride A mixture of 158 mg (0.15 mmol) of 2-cyclopropyl[1,2,4]triazolo[1,5-α]pyrazine and 100 mg of 10% palladium on carbon in ethanol (5 mL) was stirred under an atmosphere of hydrogen for 3 h. The mixture was filtered and the filtrate was concentrated to give the free base of the title compound as a yellowish solid.
LC/MS 165 (M+1).

In order to further purify this compound, 140 mg (0.854 mmol) was converted to its BOC derivative essentially following the procedure outlined in Example 2, Step A, except that no extractive work-up was performed. After evaporation of solvent, the residue was purified by flash chromatography (silica gel, eluting with a 10% to 60% ethyl acetate/hexane gradient) to give 62 mg of 7-N-(tert-butoxycarbonyl)-2-cyclopropyl-5,6,7,8-tetrahydro[1,2,4]triazolo[1,5-α]pyrazine. LS/MS 209 (M+1-tBu). The BOC group was removed according to the procedure outlined in Example 2, Step C to give the title compound. LC/MS 165 (M+1).

Step E: 7-[(3R)-3-[(tert-Butoxycarbonyl)amino]-4-(2,4,5-trifluorophenyl)butanoyl]-2-cyclopropyl-5,6,7,8-tetrahydro[1,2,4]triazolo[1,5-α]pyrazine A 54 mg portion of 2-cyclopropyl-5,6,7,8-tetrahydro[1,2,4]triazolo[1,5-α]pyrazine hydrochloride was coupled to (3R)-3-[(tert-butoxycarbonyl)amino]-4-(2,4,5-trifluorophenyl)butanoic acid essentially following the procedure outlined in Example 2, Step D. Purification by two sequential preparative TLC columns (silica gel, 10% methanol/dichloromethane) gave the title compound as a white solid.
LC/MS 380 (M+1-BOC).

Step F: 7-[(3R)-3-Amino-4-(2,4,5-trifluorophenyl)
butanoyl]-2-cyclopropyl-5,6,7,8-tetrahydro[1,2,4]
triazolo[1,5-α]pyrazine, hydrochloride The BOC protecting group was removed from a 42 mg portion of 7-[(3R)-3-[(tert-butoxycarbonyl)amino]-4-(2,4,5-trifluorophenyl)butanoyl]-2-cyclopropyl-5,6,7,8-tetrahydro[1,2,4]triazolo[1,5-α]pyrazine essentially following the procedure outlined in Example 2, Step E to provide the title compound as a white solid. LC/MS 380 (M+1).

EXAMPLE 7

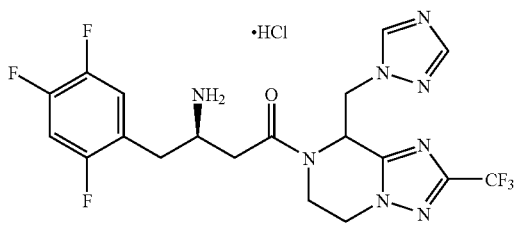

7-[(3R)-3-Amino-4-(2,4,5-trifluorophenyl)butanoyl]-
8-([1,2,4]triazol-4-ylmethyl)-2-trifluoromethyl-5,6,7,
8-tetrahydro[1,2,4]triazolo[1,5-α]pyrazine, hydro-
chloride Step A: 7-N-(tert-Butoxycarbonyl)-8-[(benzyloxy)
methyl]-2-(trifluoromethyl)-5,6,7,8 tetrahydro[1,2,4]
triazolo[1,5-α]pyrazine The title compound was prepared from 2.06 g (7.06 mmol) of 7-N-(tert-butoxycarbonyl)-2-(trifluoromethyl)-5,6,7,8-tetrahydro[1,2,4]triazolo[1,5-α]pyrazine (Example 2, Step A) and benzyl chloromethyl ether essentially following the procedure outlined in Example 2, Step B. Purification by flash chromatography (silica gel, 5 to 10% ethyl acetate/hexane gradient) gave the title compound as a white foam. LC/MS 357 (M+1-tBu).

Step B: 7-N-(tert-Butoxycarbonyl)-8-(hydroxym-
ethyl)-2-(trifluoromethyl)-5,6,7,8-tetrahydro[1,2,4]
triazolo[1,5-α]pyrazine To a solution of 733 mg (1.8 mmol) of 7-N-(tert-butoxycarbonyl)-8-[(benzyloxy)methyl]-2-(trifluoromethyl)-5,6,7,8-tetrahydro[1,2,4]triazolo[1,5-α]pyrazine in 8.0 mL of ethanol was added 400 mg of 10% palladium on carbon. The mixture was stirred under an atmosphere of hydrogen for 29 h. TLC analysis indicated that starting material was present. Thus 400 mg of 10% palladium on carbon was added and the mixture shaken on a Parr apparatus under 42 psi hydrogen for 12 h. The reaction mixture was filtered through Celite and concentrated. Flash chromatography (silica gel, 7% to 50% ethyl acetate/hexane gradient) gave the title compound as a white solid. LC/MS 267 (M+1-tBu).

Step C: 7-N-(tert-Butoxycarbonyl)-8-(methanesulfo-
nyloxymethyl)-2-(trifluoromethyl) 5,6,7,8-tetrahydro
[1,2,4]triazolo[1,5-α]pyrazine To a 0° C. solution of 100 mg (0.31 mmol) of 7-N-(tert-butoxycarbonyl)-8-(hydroxymethyl)-2-(trifluoromethyl)-5, 6,7,8-tetrahydro[1,2,4]triazolo[1,5-α]pyrazine in 1.0 mL of dichloromethane was added sequentially 0.047 mL (0.341 mmol) of triethylamine and 0.029 mL (0.372 mmol) of methanesulfonyl chloride. The reaction mixture was stirred at 0° C. and allowed to warm to room temperature for 4 h. Aqueous sodium bicarbonate solution was added, and the resultant mixture was extracted with three portions of dichloromethane. The combined organics were washed with brine, dried over magnesium sulfate, and concentrated to give a yellow oil which was used without further purification. LC/MS 401 (M+1).

Step D: 7-N-(tert-Butoxycarbonyl)-8-([1,2,4]triazol-
4-ylmethyl)-2-(trifluoromethyl)-5,6,7,8-tetrahydro[1,
2,4]triazolo[1,5-α]pyrazine To a solution of 47 mg (0.683 mmol) of [1,2,4]triazole in 1.0 mL of DMF was added 189 mg (1.365 mmol) of potassium carbonate. The mixture was heated at 50° C. for 15 min. To this was added 182 mg (0.455 mmol) of 7-N-(tert-butoxycarbonyl)-8-(methanesulfonyloxymethyl)-2-(trifluoromethyl)-5,6,7,8-tetrahydro[1,2,4]triazolo[1,5-α]pyrazine. The mixture was stirred at 50° C. for 14 h. DMF was removed in vacuo and the residue was partitioned between ethyl acetate and water. The aqueous phase was extracted with three portions of ethyl acetate. The combined organics were dried over magnesium sulfate and concentrated to give 107 mg of an orange oil. The mixture was eluted on a preparative TLC plate (silica gel, 50% ethyl acetate/hexane). The plate was scraped and the product eluted from the silica gel with 80:15:1 chloroform/methanol/ammonium hydroxide to give the title compound.

LC/MS 318 (M+1-tBu).

Step E: 7-[(3R)-3-Amino-4-(2,4,5-trifluorophenyl)
butanoyl]-8-([1,2,4]triazol-4-ylmethyl)-2-trifluorom-
ethyl-5,6,7,8-tetrahydro[1,2,4]triazolo[1,5-α]pyra-
zine Essentially following the procedures outlined in Example 2, Steps C, D and E, the title compound as a mixture of diastereomers was prepared from 69.2 mg of 7-N-(tert-butoxycarbonyl)-8-([1,2,4]triazol-4-ylmethyl)-2-(trifluoromethyl)-5,6,7,8-tetrahydro[1,2,4]triazolo[1,5-α]pyrazine. LC/MS 489 (M+1).

EXAMPLE 8

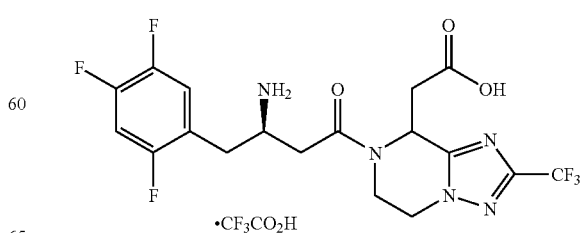

7-[(3R)-3-Amino-4-(2,4,5-trifluorophenyl)butanoyl]-8-(carboxymethyl)-2-trifluoromethyl-5,6,7,8-tetrahydro[1,2,4]triazolo[15-α]pyrazine, trifluoroacetic acid salt

Step A: 7-N-(tert-Butoxycarbonyl)-8-{2-oxo-2-[(phenylmethyl)oxy]ethyl}-2-(trifluoromethyl)-5,6,7 8-tetrahydro[1,2,4]triazolo[1,5-α]pyrazine To a solution of 1.40 g (4.79 mmol) of 7-N-(tert-butoxycarbonyl)-2-(trifluoromethyl)-5,6,7,8-tetrahydro[1,2,4]triazolo[1,5-α]pyrazine (Example 2, Step A) in 20 mL of toluene at −78° C. was added N,N,N,N-tetramethylethylenediamine (0.760 mL, 5.03 mmol) followed by n-butyllithium (2.01 mL of a 2.5M solution in hexanes, 5.03 mmol). The mixture was stirred at −78° C. for 10 min and then benzyl-2-bromoacetate (0.790 mL, 5.03 mmol) was added dropwise. The mixture was allowed to stir at −78° C. for 10 min, and then it was warmed to ambient temperature. The reaction was quenched with aqueous ammonium chloride solution, and the aqueous layer was extracted three times with ethyl acetate. The combined organic layers were washed with brine, dried over magnesium sulfate, and concentrated. Purification by flash chromatography (silica gel, 2 to 15% ethyl acetate/hexane gradient), and further reverse phase purification (Gilson, YMC C-18, 10 to 90% acetonitrile/water gradient) yielded the title compound. LC/MS 441 (M+1).

Step B: 8-{2-Oxo-2-[(phenylmethyl)oxy]ethyl}-2-(trifluoromethyl)-5,6,7,8-tetrahydro[1,2,4]triazolo[1,5-α]pyrazine, trifluoroacetic acid salt To a solution of 7-N-(tert-butoxycarbonyl)-8-{2-oxo-2-[(phenylmethyl)oxy]ethyl}-2-(trifluoromethyl)-5,6,7,8-tetrahydro[1,2,4]triazolo[1,5-α]pyrazine (0.240 g, 0.545 mmol) in 2.0 mL of dichloromethane was added 2.0 mL trifluoroacetic acid. The reaction was stirred at ambient temperature for 18 h. Concentration in vacuo gave the title compound. LC/MS 341 (M+1).

Step C: 7-[(3R)-3-[(tert-Butoxycarbonyl)amino]-4-(2,4,5-trifluorophenyl)butanoyl]-8-{2-oxo-2-[(phenylmethyl)oxy]ethyl}2-(trifluoromethyl)-5,6,7,8-tetrahydro[1,2,4]triazolo[1,5-α]pyrazine A 282 mg portion of 8-{2-oxo-2-[(phenylmethyl)oxy]ethyl}-2-(trifluoromethyl)-5,6,7,8-tetrahydro[1,2,4]triazolo[1,5-α]pyrazine, trifluoroacetic acid salt was coupled to (3R)-3-[(tert-butoxycarbonyl)amino]-4-(2,4,5-trifluorophenyl)butanoic acid essentially following the procedure outlined in Example 2, Step D with stirring for 72 h. Purification by preparative TLC (silica gel, 10% methanol/dichloromethane) followed by HPLC (OD chiralcel column, 15% isopropanol/heptane) separated the first and last eluting diastereomers. LC/MS 656 (M+1).

Step D: 7-[(3R)-3-Amino-4-(2,4,5-trifluorophenyl)butanoyl]-8-{2-oxo-2-[(phenylmethyl)oxy]ethyl}2-(trifluoromethyl)-5,6,7,8-tetrahydro[1,2,4]triazolo[1,5-α]pyrazine, trifluoroacetic acid salt To a solution of 19.7 mg (0.030 mmol) of the slower eluting diastereomer of 7-[(3R)-3-[(tert-butoxycarbonyl)amino]-4-(2,4,5-trifluorophenyl)butanoyl]-8-{2-oxo-2-[(phenylmethyl)oxy]ethyl}2-(trifluoromethyl)-5,6,7,8-tetrahydro[1,2,4]triazolo[1,5-α]pyrazine from Step C in 1 mL of dichloromethane was added 1 mL of trifluoroacetic acid. After 3 h, the reaction was concentrated in vacuo to give the title compound as clear viscous material. LC/MS 556 (M+1).

In a separate experiment, to a solution of 17.4 mg of the faster eluting diastereomer in 1 mL of dichloromethane was added 1 mL of trifluoroacetic acid. The reaction was stirred at ambient temperature for 3 h. Concentration gave the product as clear viscous material. LC/MS 556 (M+1).

Step E: 7-[(3R)-3-Amino-4-(2,4,5-trifluorophenyl)butanoyl]-8-(carboxymethyl)-2-trifluoromethyl-5,6,7,8-tetrahydro[1,2,4]triazolo[1,5-α]pyrazine, trifluoroacetic acid salt The deprotected faster eluting diastereomer of 7-[(3R)-3-Amino-4-(2,4,5-trifluorophenyl)butanoyl]-8-{2-oxo-2-[(phenylmethyl)oxy]ethyl}-2-(trifluoromethyl)-5,6,7,8-tetrahydro[1,2,4]triazolo[1,5-α]pyrazine (8.0 mg, 0.014 mmol, from Step D) was hydrogenated under 42 psi hydrogen with 10% palladium on carbon (5.0 mg) as a catalyst in methanol (1.5 mL) at ambient temperature for 18 h. Filtration through Celite followed by concentration gave the title compound as a clear viscous oil. LC/MS 466 (M+1).

In a separate experiment, the deprotected slower eluting diastereomer (5.0 mg, 0.0090 mmol, from Step D) was hydrogenated under 42 psi hydrogen with 10% palladium on carbon (2.0 mg) as a catalyst in methanol (1.5 mL) at ambient temperature for 18 h. Filtration through Celite followed by concentration gave the title compound as a clear viscous oil. LC/MS 466 (M+1).

EXAMPLE 9

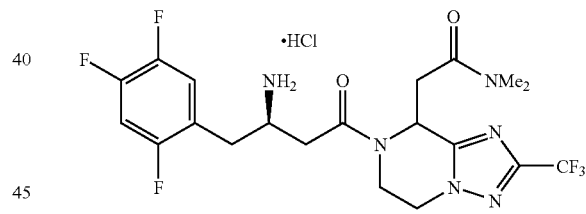

7-[(3R)-3-Amino-4-(2,4,5-trifluorophenyl)butanoyl]-8-[[(dimethylamino)carbonyl]methyl]-2-trifluoromethyl-5,6,7,8-tetrahydro[1,2,4]triazolo[1,5-α]pyrazine, hydrochloride

Step A: 2-Bromo-N,N-dimethylacetamide

To a solution of bromoacetyl bromide (13.01 g, 64.46 mmol) in dichloromethane (100 mL) was added triethylamine (18.9 mL, 135.4 mmol) dropwise at −78° C. The reaction mixture was stirred at −78° C. for 10 min and at ambient temperature for 1 h, then washed with saturated aqueous sodium bicarbonate solution followed by 2N hydrochloric acid. The organic phase was washed with brine and dried over anhydrous magnesium sulfate. Concentration followed by flash chromatography (50% ethyl acetate/hexanes, then 100% ethyl acetate) afforded the title compound as an oil. LC/MS 165.8 (M+1), 167.8 (M+3).

Step B: 7-N-(tert-Butoxycarbonyl)-8-[2-(dimethylamino)-2-oxoethyl]-2-(trifluoromethyl)-5,6,7,8-tetrahydro[1,2,4]triazolo[1,5-α]pyrazine To a solution of 2.13 g (7.30 mmol) of 7-N-(tert-butoxycarbonyl)-2-(trifluoromethyl)-5,6,7,8-tetrahydro[1,2,4]triazolo[1,5-α]pyrazine (Example 2, Step A) in 10 mL of tetrahydrofuran at −78° C. was added lithium diisopropylamide (4.02 mL of a 2.0M solution in heptane/tetrahydrofuran/ethylbenzene, 8.03 mmol). The mixture was allowed to stir at −78° C. for 15 min, and then 2-bromo-N,N-dimethylacetamide from Step A in 5 mL of tetrahydrofuran was added, and the mixture slowly warmed to ambient temperature over 18 h. The reaction was quenched with aqueous ammonium chloride and the aqueous layer was extracted three times with ethyl acetate. The combined organic layers were washed with brine, dried over magnesium sulfate, and concentrated. Purification by flash chromatography (silica gel, gradient of 50% to 75% ethyl acetate/hexane) yielded the title compound. LC/MS 322 ((M+1)-t-butyl).

Step C: 8-[2-(dimethylamino)-2-oxoethyl]-2-(trifluoromethyl)-5,6,7,8-tetrahydro[1,2,4]triazolo[1,5-α]pyrazine, hydrochloride 7-N-(tert-butoxycarbonyl)-8-[2-(dimethylamino)-2-oxoethyl]-2-(trifluoromethyl)-5,6,7,8-tetrahydro[1,2,4]triazolo[1,5-α]pyrazine (630 mg, 1.67 mmol) was dissolved in 5 mL of methanol saturated with hydrogen chloride. The reaction was stirred at ambient temperature for 1 h. Concentration in vacuo gave the title compound as an off-white solid. LC/MS 278 (M+1).

Step D: 7-[(3R)-3-[(tert-Butoxycarbonyl)amino]-4-(2,4,5-trifluorophenyl)butanoyl]-8-[2-(dimethylamino)-2-oxoethyl]-2-(trifluoromethyl)-5,6,7,8-tetrahydro[1,2,4]triazolo[1,5-α]pyrazine A 200 mg portion of 8-[2-(dimethylamino)-2-oxoethyl]-2-(trifluoromethyl)-5,6,7,8-tetrahydro[1,2,4]triazolo[1,5-α]pyrazine, hydrochloride was coupled to (3R)-3-[(tert-butoxycarbonyl)amino]-4-(2,4,5-trifluorophenyl)butanoic acid essentially following the procedure outlined in Example 2, Step D. Purification by preparative TLC (silica gel, 10% methanol/dichloromethane) followed by HPLC (AD chiral pak column, 15% isopropanol/heptane) separated the first and last eluting diastereomers. LC/MS 593 (M+1).

Step E: 7-[(3R)-3-Amino-4-(2,4,5-trifluorophenyl)butanoyl]-8-[2-(dimethylamino)-2-oxoethyl]-2-(trifluoromethyl)-5,6,7,8-tetrahydro[1,2,4triazolo[1,5-α]pyrazine, hydrochloride To 57.7 mg (0.097 mmol) of the slower eluting diastereomer of 7-[(3R)-3-[(tert-butoxycarbonyl)amino]-4-(2,4,5-trifluorophenyl)butanoyl]-8-[2-(dimethylamino)-2-oxoethyl]-2-(trifluoromethyl)-5,6,7,8-tetrahydro[1,2,4]triazolo[1,5-α]pyrazine from Step D was added 1 mL of methanol saturated with hydrochloric acid. After 1 h, the reaction was concentrated in vacuo to give the title compound as a white solid. LC/MS 493 (M+1).

In a separate experiment, to 83 mg of the faster eluting diastereomer was added 1 mL of methanol saturated with hydrochloric acid. The reaction was stirred at ambient temperature for 1 h. Concentration gave the product as a white solid. LC/MS 493 (M+1).

EXAMPLE 10

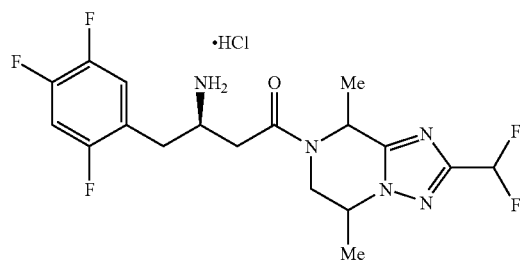

7-[(3R)-3-Amino-4-(2,4,5-trifluorophenyl)butanoyl]-5,8-dimethyl-2-difluoromethyl-5,6,7,8-tetrahydro[1,2,4]triazolo[1,5-α]pyrazine, hydrochloride

Step A: 3-Hydrazino-2,5-dimethylpyrazine

To 3-chloro-2,5-dimethylpyrazine (26.0 g, 0.182 mol) placed in a round bottom flask was added hydrazine hydrate (75 mL). The reaction mixture was refluxed for 3 h, cooled to ambient temperature, and then kept in a refrigerator for 24 h. The precipitate was collected and washed with hexanes and diethyl ether to afford the title compound as dark colored solid. The compound was used in the next step without further purification. LC/MS 138.9 (M+1); $^1$H-NMR (500 MHz, CDCl$_3$): δ 2.33 (s, 3H), 2.41 (s, 3H), 4.10 (br S, 2H), 5.75 (br s, 1H), 7.70 (s, 1H).

Step B: 3,6-Dimethylpyrazin-2-amine

To a solution of 3-hydrazino-2,5-dimethylpyrazine (2.00 g, 14.5 mmol) from Step A in 75 mL of water was added approximately 1 g (wet) Raney Ni, 50% slurry in water. After stirring at reflux for 2 h, the reaction mixture was filtered hot through Celite, and subsequently washed with hot water, followed by dichloromethane. The concentrated residues were suspended in ethylenediamine and heated at 50° C. for 30 min with stirring. Concentration followed by purification by flash chromatography (silica gel, 50% ethyl acetate/hexane) yielded the title compound. LC/MS 124 (M+1).

Step C: 2,2-Difluoro-N-(3,6-dimethylpyrazin-2-yl)acetamide

To a slightly heterogeneous solution of 3,6-dimethylpyrazin-2-amine (1.88 g, 15.3 mmol) and N,N-diisopropylethylamine (5.32 mL, 30.5 mmol) in dichloromethane (75 mL) was added difluoroacetic anhydride (3.19 g, 18.3 mmol) dropwise at 0° C. The solution was stirred at 0° C. for 10 min and at ambient temperature for 2 h. The mixture was partitioned between dichloromethane and brine. The aqueous portion was extracted with dichloromethane, washed with brine, and dried over anhydrous magnesium sulfate. Concentration gave the title compound as a brown solid. LC/MS 202 (M+1).

Step D: 2,2-Difluoro-N'-hydroxy-N-(3,6-dimethylpyrazin-2-yl)ethanimidamide

To a suspension of 2,2-difluoro-N-(3,6-dimethylpyrazin-2-yl)acetamide (4.65 g, 23.1 mmol, from Step C) in 1,2-dichloroethane (55 mL) was added phosphorous pentachloride (7.23 g, 34.7 mmol) portionwise. The mixture was refluxed for 20 h. After evaporation of dichloroethane, the residue was suspended in tetrahydrofuran (55 mL). To the above mixture was added 50% aqueous hydroxylamine (5 m]L) dropwise. After stirring at ambient temperature for 1 h, the mixture was partitioned between ethyl acetate and aqueous sodium bicarbonate. The aqueous layer was extracted three times with ethyl acetate. The combined organic layers were washed with brine and dried over anhydrous magnesium sulfate. Concentration gave the title compound as a yellow solid. LC/MS 217 (M+1).

Step E: 2-(Difluoromethyl)-5,8-dimethyl[1,2,4]triazolo[1,5-α]pyrazine

A mixture of 2,2-difluoro-N'-hydroxy-N-(3,6-dimethylpyrazin-2-yl)ethanimidamide (3.05 g, 14.1 mmol, from Step D) and superphosphoric acid (100 mL) was heated to 130° C. with stirring for 18 h. The solution was added to ice and neutralized by addition of ammonium hydroxide. The dark aqueous solution was extracted three times with ethyl acetate, washed with brine, and dried over anhydrous magnesium sulfate. Concentration followed by flash chromatography (35% ethyl acetate/hexane) afforded the title compound as a yellow solid. LC/MS 199 (M+1).

Step F: 2-(Difluoromethyl)-5,8-dimethyl[5,6,7,8]-tetrahydro[1,2,4]triazolo[1,5-α]pyrazine 2-(Difluoromethyl)-5,8-dimethyl[1,2,4]triazolo[1,5-α]pyrazine (1.65 g, 8.33 mmol, from Step E) was hydrogenated under atmospheric hydrogen with 10% palladium on carbon (300 mg) as a catalyst in ethanol (30 mL) at ambient temperature for 18 h. As indicated by TLC, only starting material was present. After the addition of 10% palladium on carbon (500 mg), the reaction was placed on the Parr Hydrogenator under 42 psi of hydrogen with mixing for 63 h. Filtration through Celite followed by concentration gave the title compound. LC/MS 203 (M+1).

Step G: 7-[(3R)-3-[(tert-Butoxycarbonyl)amino]-4-(2,4,5-trifluorophenyl)butanoyl]-2-(difluoromethyl)-5,8-dimethyl[5,6,7,8]-tetrahydro[1,2,4]triazolo[1,5-α]pyrazine A 200-mg portion of 2-(difluoromethyl)-5,8-dimethyl[5,6,7,8]-tetrahydro[1,2,4]triazolo[1,5-α]pyrazine was coupled to (3R)-3-[(tert-butoxycarbonyl)amino]-4-(2,4,5-trifluorophenyl)butanoic acid essentially following the procedure outlined in Example 2, Step D with heating at 60° C. Purification by preparative TLC (silica gel, 10% methanol/dichloromethane) followed by HPLC (OD chiral pak column, 12% isopropanol/heptane) separated the first and last eluting diastereomers. LC/MS 418 (M+1-Boc).

Step H: 7-[(3R)-3-Amino-4-(2,4,5-trifluorophenyl)butanoyl]-2-(difluoromethyl)-5,8-dimethyl[5,6,7,8]-tetrahydro[1,2,4]triazolo[1,5-α]pyrazine, hydrochloride To 81.0 mg (0.157 mmol) of the slower eluting diastereomer of 7-[(3R)-3-[(tert-Butoxycarbonyl)amino]-4-(2,4,5-trifluorophenyl)butanoyl]-2-(difluoromethyl)-5,8-dimethyl[5,6,7,8]-tetrahydro[1,2,4]triazolo[1,5-α]pyrazine from Step G was added 2 mL of methanol saturated with hydrochloric acid. After 1 h, the reaction was concentrated in vacuo to give the title compound as a white solid. LC/MS 418 (M+1).

In a separate experiment, to 54.1 mg of the faster eluting diastereomer was added 2 mL of methanol saturated with hydrochloric acid. The reaction was stirred at ambient temperature for 1 h. Concentration gave the product as a white solid. LC/MS 418 (M+1).

Essentially following the procedures outlined for Examples 1-10, the compounds listed in Table 2 were prepared.

TABLE 2

| Example | $R^3$ | $R^8$ | $R^1$ | MS (M + 1) |
|---|---|---|---|---|
| 11 | 2-F,5-F | H | $CF_3$ | 390 |
| 12 | 2-F,4-F,5-F | $CH_2$(4-$CF_3$—Ph) | $CF_3$ | 566 |
| 13 | 2-F,4-F,5-F | $CH_2$(4-F—Ph) | $CF_3$ | 516 |
| 14 | 3-F,4-F | $CH_2$(4-F—Ph) | $CF_3$ | 498 |
| 15 | 3-F,4-F | CHOH(cPr) | $CF_3$ | 460 |
| 16 | 2-F,4-F,5-F | H | $CF_3$ | 340 |
| 17 | 2-F,4-F,5-F | $CH_2OCH_2Ph$ | $CF_3$ | 528 |
| 18 | 3-F,4-F | $CH_2$(1,2,4-triazol-1-yl) | $CF_3$ | 471 |
| 19 | 2-F,4-F,5-F | $CH_2$(imidazol-1-yl) | $CF_3$ | 488 |
| 20 | 2-F,4-F,5-F | $CH_2$(pyrazol-1-yl) | $CF_3$ | 488 |
| 21 | 2-F,5-F | Me | $CF_3$ | 404 |
| 22 | 2-F,4-F,5-F | $CH_2CO_2CH_2Ph$ | $CF_3$ | 556 |
| 23 | 2-F,4-F,5-F | H | $CHF_2$ | 390 |
| 24 | 2-F,4-F,5-F | Me | $CHF_2$ | 404 |
| 25 | 2-F,4-F,5-F | $CH_2OMe$ | $CF_3$ | 452 |

Example of a Pharmaceutical Formulation

As a specific embodiment of an oral pharmaceutical composition, a 100 mg potency tablet is composed of 100 mg of any of the compounds of the present invention, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the formula I:

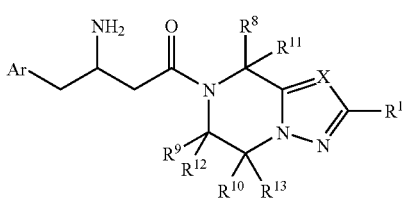

or a pharmaceutically acceptable salt thereof; wherein
each n is independently 0, 1, or 2;
X is N;
Ar is phenyl substituted with one to five $R^3$ substituents;
$R^1$ and $R^2$ are each independently selected from the group consisting of
  hydrogen,
  halogen,
  cyano,
  $C_{1-10}$ alkyl, wherein alkyl is unsubstituted or substituted with one to five halogens,
  $C_{1-10}$ alkoxy, wherein alkoxy is unsubstituted or substituted with one to five substituents independently selected from halogen or hydroxy,
  $C_{1-10}$ alkylthio, wherein alkylthio is unsubstituted or substituted with one to five substituents independently selected from halogen or hydroxy,
  $C_{2-10}$ alkenyl, wherein alkenyl is unsubstituted or substituted with one to five substituents independently selected from halogen or hydroxy,
  $(CH_2)_n COOH$,
  $(CH_2)_n COOC_{1-6}$ alkyl,
  $(CH_2)_n CONR^4 R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
  or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
  $(CH_2)_n$—$NR^4 R^5$,
  $(CH_2)_n$—$OCONR^4 R^5$,
  $(CH_2)_n$—$SO_2 NR^4 R^5$,
  $(CH_2)_n$—$SO_2 R^6$,
  $(CH_2)_n$—$NR^7 SO_2 R^6$,
  $(CH_2)_n$—$NR^7 CONR^4 R^5$,
  $(CH_2)_n$—$NR^7 COR^7$,
  $(CH_2)_n$—$NR^7 CO_2 R^6$,
  $(CH_2)_n$—$COR^6$,
  $(CH_2)_n$-aryl, wherein aryl is unsubstituted or substituted with one to five substituents independently selected from halogen, CN, hydroxy, $NR^7 SO_2 R^6$, $SO_2 R^6$, $CO_2 H$, $C_{1-6}$ alkyloxycarbonyl, $C_{1-6}$ alkyl and $C_{1-6}$ alkoxy, wherein alkyl and alkoxy are unsubstituted or substituted with one to five substituents independently selected from halogen, $CO_2 H$, and $C_{1-6}$ alkyloxycarbonyl,
  $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens,
  $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
  $(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens; and
  wherein any methylene ($CH_2$) carbon atom in $R^1$ or $R^2$ is unsubstituted or substituted with one to two groups independently selected from halogen, hydroxy, and $C_{1-4}$ alkyl unsubstituted or substituted with one to five halogens;
each $R^3$ is independently selected from the group consisting of
  hydrogen,
  halogen,
  cyano,
  hydroxy,
  $C_{1-6}$ alkyl, unsubstituted or substituted with one to five halogens, and
  $C_{1-6}$ alkoxy, unsubstituted or substituted with one to five halogens;
$R^6$ is independently selected from the group consisting of tetrazolyl, thiazolyl, $(CH_2)_n$-phenyl, $(CH_2)_n$-$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $R^6$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;
each $R^7$ is hydrogen or $R^6$;
$R^8$, $R^9$, $R^{10}$, $R^{11}$, $R^{12}$, and $R^{13}$ are each independently selected from the group consisting of:
  hydrogen,
  cyano,
  $(CH_2)_n COOH$,
  $(CH_2)_n COOC_{1-6}$ alkyl, wherein alkyl is unsubstituted or substituted with one to three substituents independently selected from halogen and phenyl,
  $C_{1-10}$ alkyl, unsubstituted or substituted with one to five substituents independently selected from halogen, hydroxy, $C_{1-6}$ alkoxy, carboxy, $C_{1-6}$ alkyloxycarbonyl, and phenyl-$C_{1-3}$ alkoxy, wherein alkoxy is unsubstituted or substituted with one to five halogens,
  $(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens, $(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n CONR^4 R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or wherein $R^4$ and $R^5$ together with the nitrogen atom to which they are attached form a heterocyclic ring selected from azetidine, pyrrolidine, piperidine, piperazine and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; and wherein any methylene ($CH_2$) carbon atom in $R^8$, $R^9$, $R^{10}$, $R^{11}$, $R^{12}$, or $R^{13}$ is unsubstituted or substituted with one to two groups independently selected from halogen, hydroxy, and $C_{1-4}$ alkyl unsubstituted or substituted with one to five halogens.

2. The compound of claim 1 of the formula Ia:

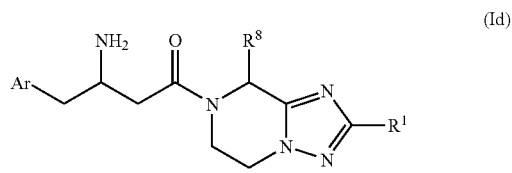

(Ia)

wherein the carbon atom marked with an * has the R configuration and Ar, X, $R^1$, $R^8$, $R^9$, $R^{10}$, $R^{11}$, $R^{12}$, and $R^{13}$ are as defined in claim 1.

3. The compound of claim 2 of the formula Ic:

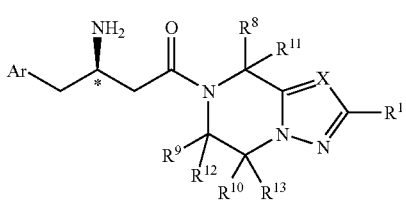

(Ic)

wherein the carbon atom marked with an * has the R configuration and Ar, $R^1$, $R^8$, $R^9$, $R^{10}$, $R^{11}$, $R^{12}$, and $R^{13}$ are as defined in claim 1.

4. The compound of claim 2 of the formula Id:

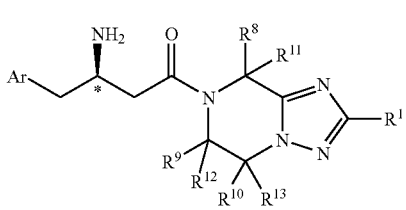

(Id)

wherein Ar, $R^1$, and $R^8$ are as defined in claim 1.

5. The compound of claim 1 wherein $R^3$ is selected from the group consisting of hydrogen, fluoro, chloro, bromo, trifluoromethyl, and methyl.

6. The compound of claim 5 wherein $R^3$ is selected from the group consisting of hydrogen, fluoro, and chloro.

7. The compound of claim 6 wherein $R^3$ is hydrogen or fluoro.

8. The compound of claim 1 wherein $R^1$ is selected from the group consisting of:
hydrogen,
$C_{1-6}$ alkyl, wherein alkyl is unsubstituted or substituted with one to five fluorines,
$(CH_2)_n$-phenyl wherein phenyl is unsubstituted or substituted with one to five substituents independently selected from hydroxy, halogen, $C_{1-6}$ alkyl, $C_{1-6}$ alkoxy, wherein alkyl and alkoxy are unsubstituted or substituted with one to five halogens,
$C_{3-6}$ cycloalkyl, unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; and wherein any methylene ($CH_2$) carbon atom in $R^1$ is unsubstituted or substituted with one to two groups independently selected from halogen, hydroxy, and $C_{1-4}$ alkyl unsubstituted or substituted with one to five halogens.

9. The compound of claim 8 wherein $R^1$ is selected from the group consisting of
hydrogen,
methyl,
ethyl,
difluoromethyl,
trifluoromethyl,
$CH_2CF_3$,
$CF_2CF_3$,
phenyl, and
cyclopropyl.

10. The compound of claim 9 wherein $R^1$ is selected from the group consisting of hydrogen, difluoromethyl, trifluoromethyl, phenyl, and cyclopropyl.

11. The compound of claim 1 wherein $R^2$ is selected from the group consisting of
hydrogen,
$C_{1-6}$ alkyl, unsubstituted or substituted with one to five fluorines,
phenyl, unsubstituted or substituted with one to three substituents independently selected from fluoro, chloro, trifluoromethyl, methoxy, and $OCF_3$, and
$C_{3-6}$ cycloalkyl, unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens.

12. The compound of claim 11 wherein $R^2$ is selected from the group consisting of hydrogen, trifluoromethyl, phenyl, and cyclopropyl.

13. The compound of claim 12 wherein $R^2$ is hydrogen or trifluoromethyl.

14. The compound of claim 1 wherein $R^{11}$, $R^{12}$, and $R^{13}$ are each hydrogen and $R^8$, $R^9$, and $R^{10}$ are each independently selected from the group consisting of:

hydrogen, $C_{1-6}$ alkyl, unsubstituted or substituted with one to five substituents independently selected from halogen, hydroxy, $C_{1-6}$ alkoxy, and phenyl-$C_{1-3}$ alkoxy, wherein alkoxy is unsubstituted or substituted with one to five halogens, $(CH_2)_n COOH$, $(CH_2)_n COOC_{1-6}$ alkyl, wherein alkyl is unsubstituted or substituted with one to three substituents independently selected from halogen and phenyl, $(CH_2)_n CONR^4R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or wherein $R^4$ and $R^5$ together with the nitrogen atom to which they are attached form a heterocyclic ring selected from azetidine, pyrrolidine, piperidine, piperazine and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-phenyl, wherein phenyl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens, $(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are optionally substituted with one to five halogens; and wherein any methylene ($CH_2$) carbon atom in $R^8$, $R^9$ or $R^{10}$ is unsubstituted or substituted with one to two groups independently selected from halogen, hydroxy, and $C_{1-4}$ alkyl unsubstituted or substituted with one to five halogens.

15. The compound of claim 14 wherein $R^8$, $R^9$, and $R^{10}$ are each independently selected from the group consisting of:

hydrogen, $C_{1-3}$ alkyl, unsubstituted or substituted with one to three substituents independently selected from halogen, hydroxy, $C_{1-6}$ alkoxy, and phenyl-$C_{1-3}$ alkoxy, wherein alkoxy is unsubstituted or substituted with one to five halogens, $(CH_2)_n COOH$, $(CH_2)_n COOC_{1-6}$ alkyl, wherein alkyl is unsubstituted or phenyl, $(CH_2)_n CONR^4R^5$, wherein $R^4$ and $R^5$ are independently selected from the group consisting of hydrogen and $C_{1-6}$ alkyl, wherein alkyl is unsubstituted or substituted with one to five halogens;

or wherein $R^4$ and $R^5$ together with the nitrogen atom to which they are attached form a heterocyclic ring selected from azetidine, pyrrolidine, piperidine, piperazine and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-phenyl, wherein phenyl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, herein alkyl and alkoxy are optionally substituted with one to five halogens, $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are optionally substituted with one to five halogens, $(CH_2)_n$—$C_{3-6}$ cyclopropyl; and wherein any methylene ($CH_2$) carbon atom in $R^8$, $R^9$ or $R^{10}$ is unsubstituted or substituted with one to two groups independently selected from halogen, hydroxy, and $C_{1-4}$ alkyl unsubstituted or substituted with one to five halogens.

16. The compound of claim 15 wherein $R^8$, $R^9$, and $R^{10}$ are each independently selected from the group consisting of:

hydrogen, $CH_3$, $CH_2CH_3$, $CH_2$-cyclopropyl,

CHF-cyclopropyl,

CH(OH)-cyclopropyl, $CH_2OCH_2Ph$, $CH_2$(4-F-Ph), $CH_2$(4-$CF_3$-Ph), $CH_2$-[1,2,4]triazol-4-yl, $CH_2$-(imidazol-1-yl), $CH_2$-(pyrazol-1-yl), $CH_2$—$COOCH_2Ph$, $CH_2$—COOH, $CH_2$—$CONMe2$, and $CH_2OCH_3$.

17. The compound of claim 16 wherein $R^9$ and $R^{10}$ are each independently hydrogen or methyl.

18. The compound of claim 3 which is selected from the group consisting of:

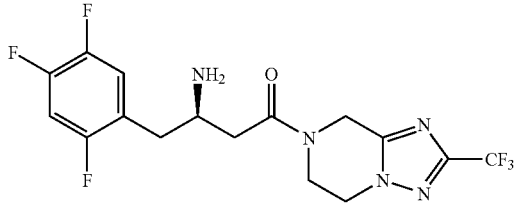
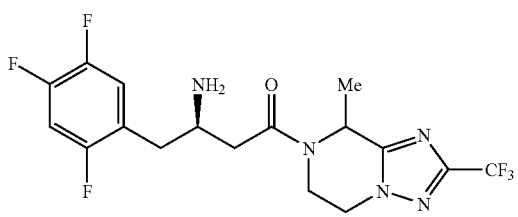
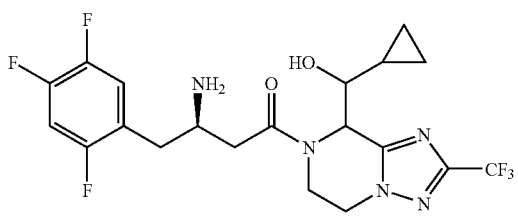
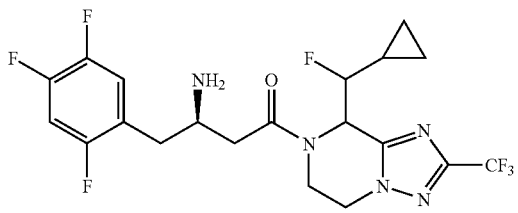
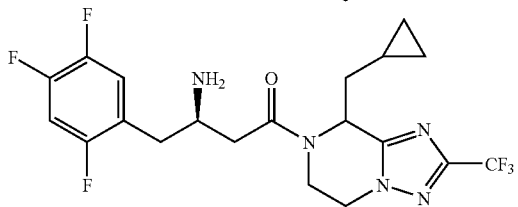
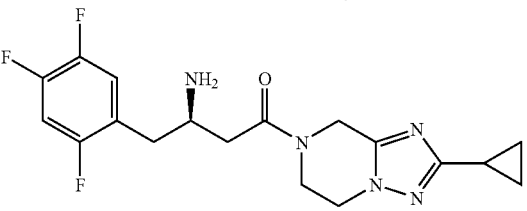
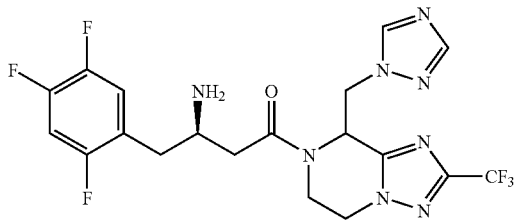

-continued

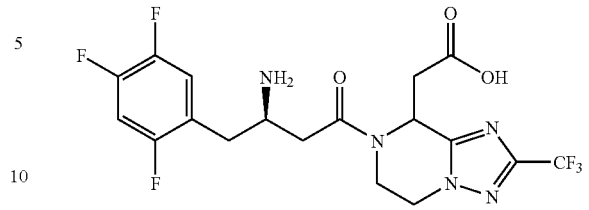
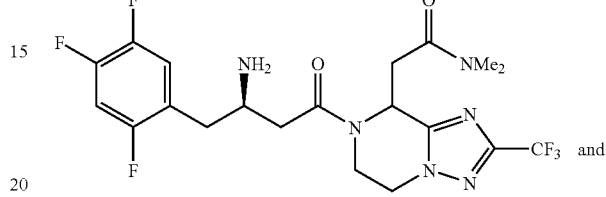
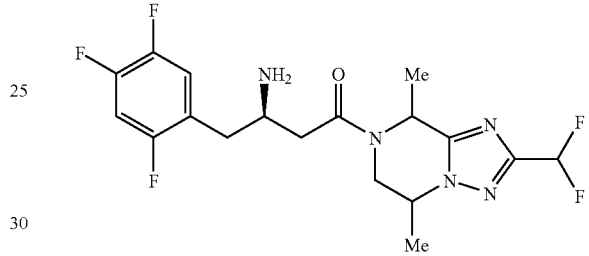

wherein Me represent a methyl radical;
or a pharmaceutically acceptable salt thereof.

19. The compound of claim 3 of the structural formula selected from the group consisting of:

| $R^3$ | $R^8$ | $R^1$ |
|---|---|---|
| 2-F,5-F | H | $CF_3$ |
| 2-F,4-F,5-F | $CH_2$(4-$CF_3$—Ph) | $CF_3$ |
| 2-F,4-F,5-F | $CH_2$(4-F—Ph) | $CF_3$ |
| 3-F,4-F | $CH_2$(4-F—Ph) | $CF_3$ |
| 3-F,4-F | CHOH(cyclopropyl) | $CF_3$ |
| 2-F,4-F,5-F | H | $CF_3$ |
| 2-F,4-F,5-F | $CH_2OCH_2Ph$ | $CF_3$ |
| 3-F,4-F | $CH_2$(1,2,4-triazol-1-yl) | $CF_3$ |
| 2-F,4-F,5-F | $CH_2$(imidazol-1-yl) | $CF_3$ |
| 2-F,4-F,5-F | $CH_2$(pyrazol-1-yl) | $CF_3$ |
| 2-F,5-F | Me | $CF_3$ |
| 2-F,4-F,5-F | $CH_2CO_2CH_2Ph$ | $CF_3$ |
| 2-F,4-F,5-F | H | $CHF_2$ |
| 2-F,4-F,5-F | Me | $CHF_2$ |
| 2-F,4-F,5-F | $CH_2OMe$ | $CF_3$. | wherein Me represent a methyl radical;
or a pharmaceutically acceptable salt thereof.

20. A pharmaceutical composition which comprises a compound of claim 1 and a pharmaceutically acceptable carrier.

21. A method for treating or controlling non-insulin dependent (Type 2) diabetes in a mammal in need thereof which comprises the administration to the mammal of a therapeutically effective amount of a compound of claim 1.

22. The pharmaceutical composition of claim 20 further comprising one or more additional active ingredients selected from the group consisting of:
(a) a second dipeptidyl peptidase IV inhibitor;
(b) an insulin sensitizer selected from the group consisting of a PPARγ agonist, a PPARα/γ dual agonist, a PPARα agonist, a biguanide, and a protein tyrosine phosphatase-1B inhibitor;
(c) an insulin or insulin mimetic;
(d) a sulfonylurea or other insulin secretagogue;
(e) an α-glucosidase inhibitor;
(f) a glucagon receptor antagonist;
(g) GLP-1, a GLP-1 mimetic, or a GLP-1 receptor agonist;
(h) PACAP, a PACAP mimetic, or a PACAP receptor agonist;
(i) a cholesterol lowering agent selected from the group consisting of (i) HMG-CoA reductase inhibitor, (ii) sequestrant, (iii) nicotinyl alcohol, nicotinic acid or a salt thereof, (iv) PPARα agonist, (v) PPARα/γ dual agonist, (vi) inhibitor of cholesterol absorption, (vii) acyl CoA:cholesterol acyltransferace inhibitor, and (viii) anti-oxidant;
(j) a PPARδ agonist;
(k) an antiobesity compound;
(l) an ileal bile acid transporter inhibitor; and
(m) an anti-inflammatory agent.

* * * * *